US011324804B2

(12) United States Patent
Lozano Soto et al.

(10) Patent No.: US 11,324,804 B2
(45) Date of Patent: May 10, 2022

(54) COMBINED CD6 AND IMIPENEM THERAPY FOR TREATMENT OF INFECTIOUS DISEASES AND RELATED INFLAMMATORY PROCESSES

(71) Applicant: Sepsia Therapeutics, S.L., Barcelona (ES)

(72) Inventors: Francisco Lozano Soto, Barcelona (ES); Mario Martinez Florensa, Barcelona (ES)

(73) Assignee: Sepsia Therapeutics, S.L., Barcelona (ES)

( * ) Notice: Subject to any disclaimer, the term of this patent is extended or adjusted under 35 U.S.C. 154(b) by 0 days.

(21) Appl. No.: 16/462,099

(22) PCT Filed: Nov. 17, 2017

(86) PCT No.: PCT/EP2017/079654
§ 371 (c)(1),
(2) Date: May 17, 2019

(87) PCT Pub. No.: WO2018/091679
PCT Pub. Date: May 24, 2018

(65) Prior Publication Data
US 2020/0289612 A1    Sep. 17, 2020

(30) Foreign Application Priority Data

Nov. 18, 2016 (EP) ..................... 16382540

(51) Int. Cl.
*A61K 38/17* (2006.01)
*A61P 31/00* (2006.01)
*A61K 31/198* (2006.01)
*A61K 31/407* (2006.01)

(52) U.S. Cl.
CPC .......... *A61K 38/177* (2013.01); *A61K 31/198* (2013.01); *A61K 31/407* (2013.01); *A61P 31/00* (2018.01)

(58) Field of Classification Search
None
See application file for complete search history.

(56) References Cited

U.S. PATENT DOCUMENTS

| | | | | |
|---|---|---|---|---|
| 6,900,013 | B1* | 5/2005 | Wang | C12Q 1/6837 435/287.2 |
| 7,745,391 | B2* | 6/2010 | Mintz | A61P 31/00 514/19.3 |
| 8,404,633 | B2* | 3/2013 | Lozano Soto | C07K 14/70596 514/1.1 |
| 8,691,752 | B2* | 4/2014 | Sarrias | A61K 38/1774 514/1.4 |
| 9,445,582 | B2* | 9/2016 | Lozano Soto | A01K 67/0278 |
| 10,080,785 | B2* | 9/2018 | Ballance | A61P 5/40 |
| 2004/0152780 | A1 | 8/2004 | Kumar et al. | |
| 2005/0042202 | A1 | 2/2005 | Weiner et al. | |
| 2007/0083334 | A1* | 4/2007 | Mintz | A61P 29/00 702/19 |
| 2010/0105622 | A1* | 4/2010 | Sarrias | A61P 31/04 514/1.1 |
| 2011/0245090 | A1* | 10/2011 | Abbas | C12N 9/2417 506/7 |
| 2013/0165332 | A1* | 6/2013 | Abbas | G01N 33/564 506/9 |
| 2014/0018250 | A1* | 1/2014 | Abbas | G01N 33/564 506/9 |
| 2014/0215644 | A1* | 7/2014 | Lozano Soto | A61K 39/39 800/10 |
| 2014/0371086 | A1* | 12/2014 | Abbas | C07K 14/47 506/9 |
| 2020/0289612 | A1* | 9/2020 | Lozano Soto | A61K 38/177 |

FOREIGN PATENT DOCUMENTS

| | | | | |
|---|---|---|---|---|
| CA | 2681828 | A1 * | 10/2008 | ......... A61K 38/1774 |
| CA | 3044334 | A1 * | 5/2018 | ............. A61P 31/00 |
| EP | 1654278 | A2 * | 5/2006 | ............. A61P 37/06 |
| EP | 2 143 436 | | 1/2010 | |
| EP | 2714066 | A1 * | 4/2014 | ......... A01K 67/0275 |
| EP | 3541407 | A1 * | 9/2019 | ........... A61K 31/407 |
| WO | WO-2005051988 | A2 * | 6/2005 | ............. A61P 17/06 |
| WO | WO-2012160215 | A1 * | 11/2012 | ............. A61P 37/04 |
| WO | WO-2018091679 | A1 * | 5/2018 | ........... A61K 31/407 |
| WO | WO-2019175261 | A1 * | 9/2019 | ........... A61K 38/177 |

OTHER PUBLICATIONS

Aibar et al, Journal of Critical Care, 2015, 30:914-919 (Year: 2015).*
Arman et al, Molecular Immunology. 2009, 46:2226-2235. available online: May 14, 2009 (Year: 2009).*
Bowen et al, Journal of Immunology. 1997, 158:1149-1156 (Year: 1997).*
Martinez-Florensa et al, Eur. J. Immunol, 2009, p. S61, Abstract# PA03/34 Abstract Only (Year: 2009).*
Martinez-Florensa et al, Antimicrobial Agents and Chemotherapy, Jan. 2017, vol. 61, Issue 1. 61:e01391-16 (Year: 2017).*
Martinez-Florensa et al, Frontiers in Immunology, Apr. 2018, vol. 9, Article 627. 11 pages.published: Apr. 12, 2018 (Year: 2018).*
Ruth et al, JCI Insight, 2021, 6/5:e 145662. 17 pages, published: Mar. 8, 2021 (Year: 2021).*
Cohen, "Non-antibiotic strategies for sepsis," *Clin. Microbiol. Infect.* 15:302-307, 2009.
Delano et al., "Sepsis-induced immune dysfunction: can immune therapies reduce mortality?," *J. Clin. Invest.* 126(1):23-31, 2016, (10 pages).

(Continued)

*Primary Examiner* — Nita M. Minnifield
(74) *Attorney, Agent, or Firm* — Seed Intellectual Property Law Group LLP

(57) ABSTRACT

The present invention relates to the field of medicine and provides compositions and kits-of-parts comprising a CD6 product and Imipenem, in particular for their use in a therapeutic and/or preventive method of treatment, in a mammal including a human, of an infectious disease, or of an inflammatory condition related to an infectious disease, or of an inflammatory disease related to the presence of a product derived from an infectious agent.

17 Claims, 7 Drawing Sheets

Specification includes a Sequence Listing.

(56) References Cited

OTHER PUBLICATIONS

Dziarski et al., "Binding of Bacterial Peptidoglycan to CD14," *The Journal of Biological Chemistry* 273(15):8680-8690, 1998. (12 pages).
Fink et al., "Strategies to improve drug development for sepsis," *Drug Discovery* 13:741-758, 2014.
Gimferrer et al., "Relevance of CD6-Mediated Interactions in T Cell Activation and Proliferation," *The Journal of Immunology* 173:2262-2270, 2004. (10 pages).
Janeway, Jr. et al., "Innate Immune Recognition," *Annu. Rev. Immunol.* 20:197-216, 2002. (22 pages).
Lecomte et al., "Molecular linkage of the mouse CD5 and CD6 genes," *Immunogenetics* 44(5):385-390, 1996.
Martínez-Florensa et al., "Targeting of Key Pathogenic Factors From Gram-Positive Bacteria by the Soluble Ectodomain of the Scavenger-Like Lymphocyte Receptor CD6," *The Journal of Infectious Diseases* 209:1077-1086, 2014.
Okeke et al., "In Search of a Cure for Sepsis: Taming the Monster in Critical Care Medicine," *J. Innate. Immun.* 8:156-170, 2016.
Palm et al., "Pattern recognition receptors and control of adaptive immunity," *Immunological Reviews* 227:221-233, 2009.
Papp-Wallace et al., "Carbapenems: Past, Present, and Future," *Antimicrobial Agents and Chemotherapy* 55(11):4943-4960, 2011.
Santos et al., "Tuning T Cell Activation: The Function of CD6 At the Immunological Synapse and in T Cell Responses," *Current Drug Targets* 17:630-639, 2016.
Sarrias et al., "CD6 binds to pathogen-associated molecular patterns and protects from LPS-induced septic shock," *PNAS* 104(28):11724-11729, 2007.
Sarrias et al., "The Scavenger Receptor Cysteine-Rich (SRCR) Domain: An Ancient and Highly Conserved Protein Module of the Innate Immune System," *Critical Reviews in Immunology* 24(1):1-38, 2004.
Soldevila et al., "The immunomodulatory properties of the CD5 lymphocyte receptor in health and disease," *Current Opinion in Immunology* 23:310-318, 2011.
Tobias et al., "Lipopolysaccharide Binding Protein-mediated Complexation of Lipopolysaccharide with Soluble CD14," *The Journal of Biological Chemistry* 270(18):10482-10488, 1995.
Florensa, "Additive beneficial effects of soluble CD6 forms and bactericidal antibiotics in experimental polymicrobial sepsis," *Paper Poster Session*, Apr. 9, 2016 (2 pages).
Ghosh et al., "Impaired imipenem uptake associated with alterations in outer membrane proteins and lipopolysaccharides in imipenem-resistant *Shigella dysenteriae*," *Journal of Antimicrobial Chemotherapy* 43:195-201, 1999.
Ishii et al., "Lipopolysaccharide promoted opening of the porin channel," *Federation of European Biochemical Societies* 320(3):251-255, 1993.
McInerney et al., "Quantitation of polymyxin-lipopolysaccharide interactions using an image-based fluorescent probe," *J Pharm Sci.* 105(2):1006-1010, Feb. 2016, HHS Public Access J Pharm Sci. Author manuscript available in PMC Feb. 1, 2017 (12 Pages).

\* cited by examiner

A

B

SEQUENCE LISTING

<160> NUMBER OF SEQ ID NOS: 4

<210> SEQ ID NO 1
<211> LENGTH: 373
<212> TYPE: PRT
<213> ORGANISM: Homo sapiens

<400> SEQUENCE: 1

Asp Gln Leu Asn Thr Ser Ser Ala Glu Ser Glu Leu Trp Glu Pro Gly
1               5                   10                  15

Glu Arg Leu Pro Val Arg Leu Thr Asn Gly Ser Ser Ser Cys Ser Gly
            20                  25                  30

Thr Val Glu Val Arg Leu Glu Ala Ser Trp Glu Pro Ala Cys Gly Ala 35                  40                  45

Leu Trp Asp Ser Arg Ala Ala Glu Ala Val Cys Arg Ala Leu Gly Cys
 50                  55                  60

Gly Gly Ala Glu Ala Ala Ser Gln Leu Ala Pro Thr Pro Glu Leu
 65                  70                  75                  80

Pro Pro Pro Ala Gly Asn Thr Ser Val Ala Ala Asn Ala Thr
                 85                  90                  95

Leu Ala Gly Ala Pro Ala Leu Leu Cys Ser Gly Ala Glu Trp Arg Leu
                100                 105                 110

Cys Glu Val Val Glu His Ala Cys Arg Ser Asp Gly Arg Arg Ala Arg
                115                 120                 125

Val Thr Cys Ala Glu Asn Arg Ala Leu Arg Leu Val Asp Gly Gly
                130                 135                 140

Ala Cys Ala Gly Arg Val Glu Met Leu Glu His Gly Glu Trp Gly Ser
145                 150                 155                 160

Val Cys Asp Asp Thr Trp Asp Leu Glu Asp Ala His Val Val Cys Arg
                165                 170                 175

Gln Leu Gly Cys Gly Trp Ala Val Gln Ala Leu Pro Gly Leu His Phe
                180                 185                 190

Thr Pro Gly Arg Gly Pro Ile His Arg Asp Gln Val Asn Cys Ser Gly
                195                 200                 205

Ala Glu Ala Tyr Leu Trp Asp Cys Pro Gly Leu Pro Gly Gln His Tyr
210                 215                 220

Cys Gly His Lys Glu Asp Ala Gly Val Val Cys Ser Glu His Gln Ser
225                 230                 235                 240

Trp Arg Leu Thr Gly Gly Ala Asp Arg Cys Glu Gly Gln Val Glu Val
                245                 250                 255

His Phe Arg Gly Val Trp Asn Thr Val Cys Asp Ser Glu Trp Tyr Pro
                260                 265                 270

Ser Glu Ala Lys Val Leu Cys Gln Ser Leu Gly Cys Gly Thr Ala Val
                275                 280                 285

Glu Arg Pro Lys Gly Leu Pro His Ser Leu Ser Gly Arg Met Tyr Tyr
                290                 295                 300

Ser Cys Asn Gly Glu Glu Leu Thr Leu Ser Asn Cys Ser Trp Arg Phe
305                 310                 315                 320

Asn Asn Ser Asn Leu Cys Ser Gln Ser Leu Ala Ala Arg Val Leu Cys
                325                 330                 335

Ser Ala Ser Arg Ser Leu His Asn Leu Ser Thr Pro Glu Val Pro Ala
                340                 345                 350

Ser Val Gln Thr Val Thr Ile Glu Ser Ser Val Thr Val Lys Ile Glu
                355                 360                 365

Asn Lys Glu Ser Arg
    370

<210> SEQ ID NO 2
<211> LENGTH: 1122
<212> TYPE: DNA
<213> ORGANISM: Homo sapiens

<400> SEQUENCE: 2
gaccagctca acaccagcag tgcagagagt gagctctggg agccagggga gcggcttccg    60
gtccgtctga caaacgggag cagcagctgc agcgggacgg tggaggtgcg gctcgaggcg   120
tcctgggagc ccgcgtgcgg ggcgctctgg gacagccgcg ccgccgaggc cgtgtgccga   180

```
gcactgggct gcggcggggc ggaggccgcc tctcagctcg ccccgccgac ccctgagctg      240 ccgccccgc ctgcagccgg gaacaccagc gtagcagcta atgccactct ggccggggcg       300
cccgccctcc tgtgcagcgg cgccgagtgg cggctctgcg aggtggtgga gcacgcgtgc      360
cgcagcgacg ggaggcgggc ccgtgtcacc tgtgcagaga accgcgcgct gcgcctggtg      420
gacggtggcg gcgcctgcgc cggccgcgtg gagatgctgg agcatggcga gtggggatca     480
gtgtgcgatg acacttggga cctggaggac gcccacgtgg tgtgcaggca actgggctgc     540
ggctgggcag tccaggccct gcccggcttg cacttcacgc ccggccgcgg gcctatccac     600
cgggaccagg tgaactgctc gggggccgaa gcttacctgt gggactgccc ggggctgcca     660
ggacagcact actgcggcca caaagaggac gcgggcgtgg tgtgctcaga gcaccagtcc     720
tggcgcctga caggggcgc tgaccgctgc gaggggcagg tggaggtaca cttccgaggg      780
gtctggaaca cagtgtgtga cagtgagtgg tacccatcgg aggccaaggt gctctgccag     840
tccttgggct gtggaactgc ggttgagagg cccaagggc tgccccactc cttgtccggc      900
aggatgtact actcatgcaa tggggaggag ctcaccctct ccaactgctc ctggcggttc     960
aacaactcca acctctgcag ccagtcgctg gcagccaggg tcctctgctc agcttcccgg    1020
agtttgcaca atctgtccac tcccgaagtc cctgcaagtg ttcagacagt cactatagaa    1080
tcttctgtga cagtgaaaat agagaacaag gaatctcggt ag                       1122

<210> SEQ ID NO 3
<211> LENGTH: 21
<212> TYPE: DNA
<213> ORGANISM: Artificial Sequence
<220> FEATURE:
<223> OTHER INFORMATION: AAT-Forward primer

<400> SEQUENCE: 3
ccctgtttgc tcctccgata a                                               21

<210> SEQ ID NO 4
<211> LENGTH: 24
<212> TYPE: DNA
<213> ORGANISM: Artificial Sequence
<220> FEATURE:
<223> OTHER INFORMATION: AAT-Reverse primer

<400> SEQUENCE: 4
gtccgtattt aagcagtgga tcca                                            24
```

COMBINED CD6 AND IMIPENEM THERAPY FOR TREATMENT OF INFECTIOUS DISEASES AND RELATED INFLAMMATORY PROCESSES

STATEMENT REGARDING SEQUENCE LISTING

The Sequence Listing associated with this application is provided in text format in lieu of a paper copy, and is hereby incorporated by reference into the specification. The name of the text file containing the Sequence Listing is 920186_401USPC_SEQUENCE_LISTING.txt. The text file is 5.2 KB, was created on May 12, 2020, and is being submitted electronically via EFS-Web.

TECHNICAL FIELD

This invention relates to the field of medicine, and specifically to compounds of protein nature such as CD6 in combination with antibiotics for the therapeutic and/or preventive treatment of infectious diseases and of inflammatory conditions related thereto.

BACKGROUND ART

Sepsis is a life-threatening condition caused by the host response to an infectious agent, most commonly bacterial but also fungal, viral or parasitic. Sepsis is considered a dysregulated systemic inflammatory response syndrome (SIRS) caused by an infection, leading to an overwhelming and sustained pro-inflammatory state. The inability of the immune system to control such a response can end in multi-organ dysfunction (MOD) and cardiovascular collapse (septic shock) and, if unresolved, to death (Delano M J, Ward P A. 2016. Sepsis-induced immune dysfunction: can immune therapies reduce mortality? J Clin Invest 126:23-31). Such a dysfunctional host inflammatory response is triggered by conserved structures present on microbial cell walls named pathogen associated molecular patterns (PAMPs). PAMPs are essential compounds for the microbial physiology, among which there is LPS from Gram-negative (G−) bacteria, lipoteichoic acid (LTA) and peptidoglycan (PGN) from Gram-positive (G+) bacteria, β-glucan and mannan from fungi, or single/double-stranded nucleic acids from virus (Janeway C A, Medzhitov R. 2002. Innate immune recognition. Annu Rev Immunol 20:197-216.).

Sepsis can result from many causes but is typically triggered by undiagnosed and/or untreated local infections (e.g., pneumonia or peritonitis) induced either spontaneously or as a consequence of trauma, surgery, burns or by debilitating conditions such as cancer or AIDS. Sepsis usually begins with tremor, fever, falling blood pressure (septic shock), rapid breathing, rapid heart rate, and skin lesions. Within hours, sepsis may cause spontaneous clotting in blood vessels, severe hypotension, multiple organ failure, shock, gangrene and eventually death. Sepsis causes high morbidity and mortality in humans and other animals (mortality of up to 60% in severe septic patients). In the United States and Europe, 1.5 million people develop sepsis annually. 30% of these patients die after one month and a 20% after six months. In the United States, sepsis is the $10^{th}$ cause of death, which represents a mortality higher than those caused by infarct, breast cancer or lung cancer.

The most important intervention in sepsis is quick diagnosis and treatment (every hour diagnosis and treatment is delayed mortality increases by 5-10%). Diagnosing sepsis can be difficult. Some of its symptoms, such as fever, rapid pulse, and respiratory difficulty occur frequently and can be confused as being due to other disorders. Patients diagnosed with severe sepsis are usually placed in the intensive care unit (ICU) of the hospital for special treatment.

Nowadays, sepsis, severe sepsis and septic shock still remains as an unmet clinical need with an increase in occurrence predicted and a huge socioeconomic burden as a result of population aging, increase in invasive medical procedures, emergence of multidrug-resistant (MDR) bacteria, and increased prevalence of chronic diseases (Okeke E B, Uzonna J E. 2016. In Search of a Cure for Sepsis: Taming the Monster in Critical Care Medicine. J Innate Immun 8:156-70).

Detection of PAMPs is accomplished by germ-line encoded, non-clonally distributed, and non-polymorphic pattern recognition receptors (PRRs) present on immune cells. PRRs belong to different structural and functional protein receptor families (e.g., Toll like receptors, Scavenger receptors or C-type lectins), and contribute not only to pathogen detection but engagement and modulation of innate and adaptive immune responses (Palm N W, Medzhitov R. 2009. Pattern recognition receptors and control of adaptive immunity. Immunol Rev 227:221-33).

The Scavenger Receptor Cysteine-Rich superfamily (SRCR-SF) is an ancient and highly conserved group of protein receptors characterized by the presence of one or several repeats of a 90-110 amino acid-long cysteine-rich globular domain (Sarrias M R, et al., 2004. The Scavenger Receptor Cysteine-Rich (SRCR) Domain: An Ancient and Highly Conserved Protein Module of the Innate Immune System. Crit Rev Immunol 24:1-38.). In mammals, SRCR-SF members are expressed by hemopoietic and non-hemopoetic derived cells, where they display multiple functional capabilities. Although there is no unifying role for all SRCR-SF members, some of them function as PRRs. Such a group includes macrophage (SR-AI, MARCO, CD163, and Spα), epithelial (SCARA5, DMBT1, and S5D-SR-CRB), or lymphocyte (CD5 and CD6) receptors (Martínez-Florensa M, et al., 2014. Targeting of key pathogenic factors from gram-positive bacteria by the soluble ectodomain of the scavenger-like lymphocyte receptor CD6. J Infect Dis 209:1077-1086).

The CD6 glycoprotein is a lymphocyte surface receptor highly homologous to CD5, another lymphocytic member of the SRCR-SF. Both receptors are likely derived by duplication from a common ancestral gene (Lecomte O, et al., 1996. Molecular linkage of the mouse CD5 and CD6 genes. Immunogenetics 44:385-90) and are mainly expressed by T cells, and the B1a cell subset involved in the production of natural antibodies. CD6 and CD5 share a similar extracellular region composed by three tandem SRCR domains and a cytoplasmic tail suitable for signal transduction. Indeed, CD6 and CD5 are physically associated to the T-cell receptor (TCR) complex (Gimferrer I, et al., 2004. Relevance of CD6-mediated interactions in T cell activation and proliferation. J Immunol 173:2262-70), and play relevant roles in regulating T-cell developmental and activation processes (Santos R F, et al., 2016. Tuning T Cell Activation: The Function of CD6 At the Immunological 439 Synapse and in T Cell Responses. Curr Drug Targets 17:630-9; Soldevila G, et al., 2011. The immunomodulatory properties of the CD5 lymphocyte receptor in health and disease. Curr Opin Immunol 23:310-8). CD6 but not CD5 interacts with bacterial PAMPs such as LPS, LTA and PGN. The Kd of the CD6-LPS (2.69±0.32×10-8 M), CD6-LTA (0.17±0.02 μM) and CD6-PGN (1.1±0.1 nM) interactions have been determined and are similar to that reported for CD14, the main macrophage receptor for those bacterial components (Dziarski R, et al., 1998. Binding of bacterial peptidoglycan to CD14. J Biol Chem 273:8680-90; Tobias P S, et al., 1995. Lipopolysaccharide binding protein-mediated complexation of lipopolysaccharide with soluble CD14. J Biol Chem 270: 10482-8).

Accordingly, the prophylactic infusion of a recombinant soluble form of human CD6 (rshCD6) significantly reduces mortality and serum levels of pro-inflammatory cytokines (IL-1β, IL-6 and TNF-α) in mouse models of septic shock induced by G+ and G– bacterial endotoxins (LTA+PGN, and LPS, respectively), as well as whole alive bacteria (*Staphylococcus aureus, Acinetobacter baumannii*), independently of their MDR phenotype (Martínez-Florensa M, et al., 2014. Targeting of key pathogenic factors from gram-positive bacteria by the soluble ectodomain of the scavenger-like lymphocyte receptor CD6. J Infect Dis 209:1077-1086; Sarrias M-R, et al., 2007. CD6 binds to pathogen-associated molecular patterns and protects from LPS-induced septic shock. Proc Natl Acad Sci USA 104:11724-9).

Overall mortality of sepsis and septic shock still remains high (35% and 60%, respectively) despite significant advances in supportive care and availability of potent broad-spectrum antibiotics (Cohen J. 2009. Non-antibiotic strategies for sepsis. Clin Microbiol Infect 15:302-7). Although antibiotics constitute a necessary part of the treatment of sepsis, they are probably not sufficient to substantially reduce the mortality associated with MOD associated to severe sepsis and septic shock. This, together with the raise in MDR bacteria, makes mandatory the search for alternative non-antibiotic (adjunctive) strategies. Aside from improvements in supportive care, those strategies include treatments aimed at bacterial virulence factors and/or host inflammatory and immune mediators (Okeke E B, Uzonna J E. 2016. In Search of a Cure for Sepsis: Taming the Monster in Critical Care Medicine. J Innate Immun 8:156-70; Delano M J, Ward P A. 2016. Sepsis-induced immune dysfunction: can immune therapies reduce mortality? J Clin Invest 126: 23-31; Cohen J. 2009. Non-antibiotic strategies for sepsis. Clin Microbiol Infect 15:302-7; Fink M P, Warren H S. 2014. Strategies to improve drug development for sepsis. Nat Rev Drug Discov 13:741-58).

EP 2143436 discloses that intraperitoneal (i.p.) administration of rshCD6 counteracts the lethal effects caused by LPS-induced septic shock in mice, and that CD6 has therapeutic potential for the intervention of septic shock syndrome and of other inflammatory diseases related to infectious diseases.

In addition, some drug candidates in early phase of development are a Triggering Receptor Expressed on Myeloid cells-1 (TREM-1) receptor antagonist (Merck & Co Inc and BioXell SpA,); a super-antigen antagonist (Atox Bio Ltd.), a short peptide which blocks the action of a family of deadly bacterial toxins produced by *Staphylococcus aureus* and *Streptococcus pyogenes*, termed as super-antigens; Immune Regulating Hormone (IRH, Hollis-Eden Pharmaceuticals Inc.), an autoimmune and antiinflammatory drug which controls immune system and metabolic functions; and an Adenosine A1 receptor antagonist as a treatment for Gram-septicemia (Endacea Inc.). Other molecules under development are Toll-like Receptor-4 antagonists (Takeda and Eisai); anti-TNF-alfa polyclonal antibody fragment (Protherics); bovine intestine-derived alkaline phosphatase (AM-Pharma); Norathiol (Medinox), which neutralizes nitric oxide; and transgenic antithrombin III ATryn® (GTC Biotherapeutics), which received marketing approval from European regulatory authorities in 2006 and it is in late-stage clinical trials in the United States.

Other approaches have been proposed for treating sepsis, such as: anti-IL-8 antibodies (US Patent application 2003002178A), anti-IL-18 antibodies (US 20030008822A), anti-05a antibodies and C-terminal truncated C5a peptides (US 20020165138A), chemokines and chemokine fragments (US 20020155094A), a combination of protein C and BPI antibodies (US 20020044929A), COX-2 inhibitors (US 20020006915A), algae lipopolysaccharides (U.S. Pat. No. 6,534,648) and an antibody to TNF-α and an antibody to bacterial lipopolysaccharide (U.S. Pat. No. 6,315,999).

However, despite the major advances of the past several decades in the treatment of serious infections, the incidence of sepsis and mortality due to sepsis continue to increase. Therefore, it seems desirable to provide new and improved methods and compositions for the prevention and treatment of infectious diseases and of inflammatory conditions related to these infectious diseases.

SUMMARY OF THE INVENTION

The present application discloses the in vivo prophylactic and therapeutic effects of the soluble ectodomain from the scavenger-like lymphocyte receptor CD6 (sCD6), in a lethal model of polymicrobial infection of intra-abdominal origin induced by Cecal Ligation and puncture (CLP). The results show time- and dose-dependent effects of sCD6 infusion on mouse survival post-CLP induction, which are concomitant to reduced systemic inflammatory response and bacterial load. Surprisingly, both human and mouse sCD6 infusion showed improved effects on mouse survival when combined with the broad-spectrum bactericidal antibiotic Imipenem (but not other antibiotics such as antibiotics of the same or different family, e.g., Meropenem or Erythromycin).

The ectodomain of human CD6, a cell surface receptor mainly expressed by cells of the lymphoid lineage, when administered in combination with the broad-spectrum bactericidal carbapenem Imipenem, is able to significantly increase the effects of CD6 in reducing lethal effects caused by CLP-induced septic shock in mice. Accordingly, the combination therapy of CD6 and Imipenem has therapeutic potential for the intervention of septic shock syndrome and of other inflammatory diseases related to infectious diseases.

The present invention thus provides a new composition comprising a CD6 product, or a derivative thereof, or an isoform thereof, and Imipenem. In addition, the present invention provides a kit-of-parts, also referred to in the present description as to combination product and/or pharmaceutical product, comprising a CD6 product, or a derivative thereof, or an isoform thereof, and Imipenem. Further, the present invention provides the use of the new compositions and/or the new kits-of-parts of the present invention as a medicament, in particular in a therapeutic and/or preventive method of treatment, in a mammal including a human, of an infectious disease, or of an inflammatory condition related to an infectious disease, or of an inflammatory disease related to the presence of a product derived from an infectious agent.

DETAILED DESCRIPTION OF THE INVENTION

Composition

Figure 1:
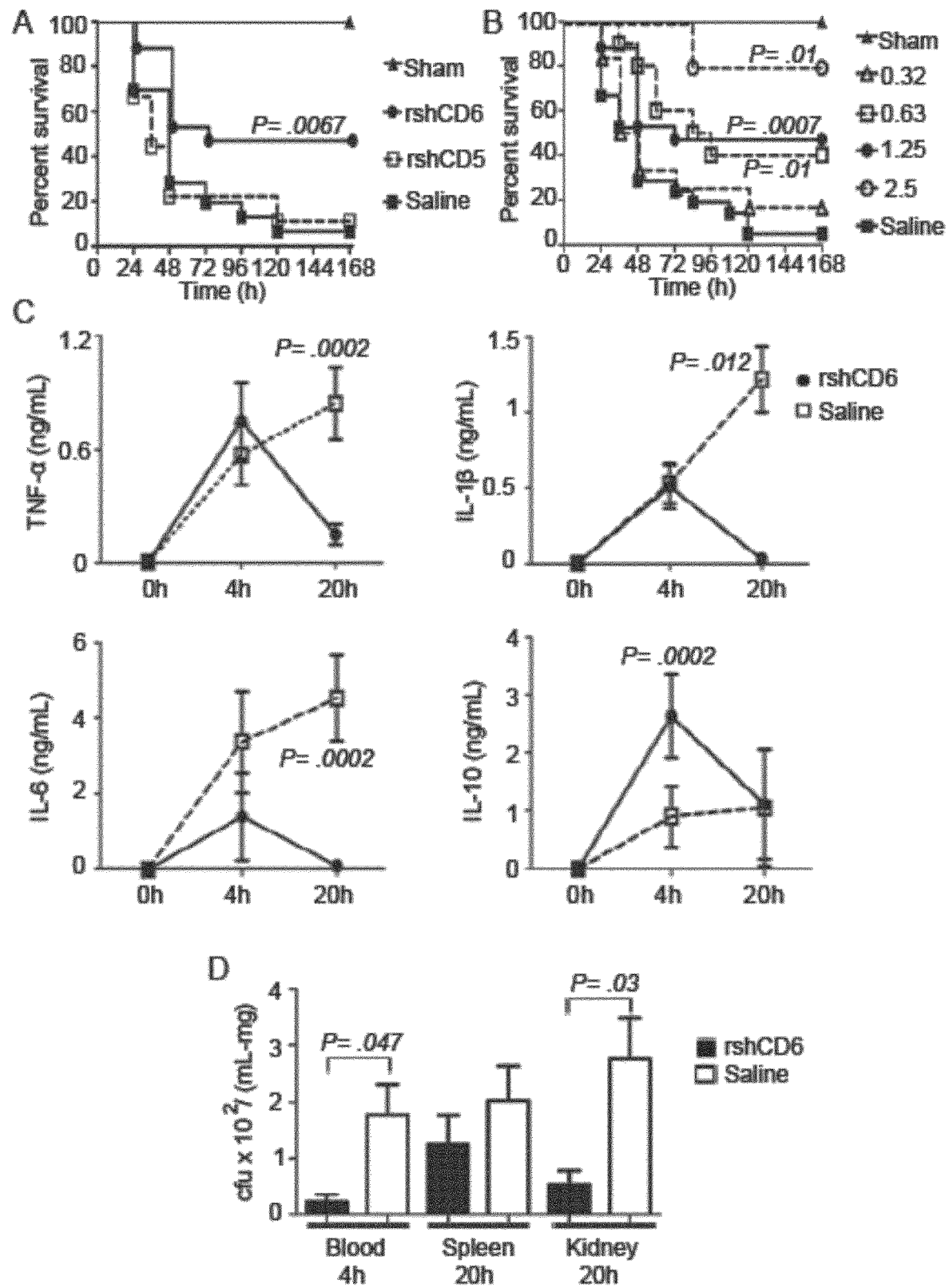
FIG. 1. Effect of prophylactic i.p. rshCD6 infusion on CLP-induced polymicrobial septic shock. A, C57BL/6J mice were infused i.p. (intraperitoneal) with saline (n=18), rshCD5 (1.25 mg/kg; n=9), or rshCDC6 (1.25 mg/kg; n=15) 1 h before induction of CLP-induced septic shock. B, C57BL/6J mice were infused with either saline (n=21) or increasing amounts of rshCD6 (0.31 mg/kg, n=12; 0.62 mg/kg, n=10; 1.25 mg/kg, n=17; or 2.50 mg/kg, n=5) 1 h before CLP-induced septic shock. In A-B, average percent of survival was analyzed over time for each group and compared to the saline treated group using the long-rank t-test. C, Plasma levels of the indicated cytokines were monitored at the indicated time points (+4 h, +20 h) post-CLP in C57BL/6J mice prophylactically treated (−1 h) with either saline (n=10) or rshCD6 (1.25 mg/kg; n=10). Data are expressed in ng or pg/mL (mean±SEM), and statistical differences evaluated using the 2-tailed Student t-test. D, Bacterial load was measured in blood, spleen and kidney at the indicated time points (+4 h, +20 h) post-CLP in C57BL/6J mice prophylactically treated (−1 h) with either saline (n=8) or rshCD6 (1.25 mg/kg; n=8). Data are expressed as cfu (colony forming units)×$10^2$/mL or mg (mean±SD), and statistical differences evaluated using a 2-tailed Student t-test.

In a first aspect, the present invention provides a composition comprising a CD6 product, or a derivative thereof, or an isoform thereof, and Imipenem ("the composition of the present invention"). The composition of the present invention can also be referred to in the present document as "combination" ("the combination of the present invention").

Preferably, the composition of the present invention is a pharmaceutical composition. As the skilled person knows, a pharmaceutical composition may comprise, in addition to the one or more active ingredients (e.g., the CD6 product, or derivative thereof, or isoform thereof, and Imipenem, in the case of the present invention), pharmaceutically acceptable carriers, pharmaceutically acceptable salts, adjuvants and/or suitable excipients. Accordingly, the pharmaceutical composition of the present invention comprises the composition of the present invention together with pharmaceutically acceptable carriers, pharmaceutically acceptable salts, adjuvants and/or suitable excipients.

As used herein, the expression "derivative of a CD6 product" includes any derivative of a CD6 product able to perform the biological function, namely any derivative of a CD6 product able to perform the same biological function as a product comprising the CD6 ectodomain or a fragment thereof. For example, a derivative of a CD6 product may be a protein or fragment thereof with at least 70% identity with SEQ ID NO.: 1. For example, a derivative of a CD6 product may be a protein or a fragment thereof with at least 70%, such as 70%, 75%, 80%, 85%, 90%, 95%, 97% or 99% identity with SEQ IDO NO.: 1, which is able to perform the same biological function as the CD6 product of the present invention.

A protein "isoform" means any of several different forms of the same protein. Different forms of a protein may be produced from related genes, or may arise from the same gene by alternative splicing, or by post-translation modifications, such as proteolytic cleavage, phosphorylation, glycosylation, etc. A large number of isoforms are also caused by single-nucleotide polymorphisms or SNPs, small genetic differences between alleles of the same gene. These occur at specific individual nucleotide positions within a gene. Alternatively, isoforms might be generated artificially by conventional molecular biology techniques. Isoform as used herein also includes fragments of a full length protein. For example, a polypeptide having at least 10%, at least 20%, at least 30%, at least 40%, at least 50%, at least 60%, at least 70%, at least 80% or at least 90% of the amino acid sequence of a (e.g. naturally occurring) full-length protein may be termed an isoform of said full-length protein. "Isoform" as used herein also includes the concept of glycoform, i.e. protein variants differing (essentially) in their glycosylation pattern, but which are able to perform the same biological function.

SEQ ID NO: 1 corresponds to a mature (fully processed) soluble isoform of human CD6. The sequence of human CD6 receptor is the one identified with the accession number P30203 (CD6_HUMAN, Last modified Dec. 15, 2009. Version 3 in the UniProtKB/Swiss-Prot database). This sequence corresponds to the receptor in the membrane isoform. It has not yet been fully determined if the soluble isoform of CD6 is also generated by proteolytical cleavage; SEQ ID NO. 1 is obtained by the addition of a stop codon in the stalk region that precedes the transmembrane region.

```
SEQ ID NO.: 1:
DQLNTSSAESELWEPGERLPVRLTNGSSSCSGTVEVRLEASWEPACGALW

DSRAAEAVCRALGCGGAEAASQLAPPTPELPPPPAAGNTSVAANATLAGA

PALLCSGAEWRLCEVVEHACRSDGRRARVTCAENRALRLVDGGGACAGRV

EMLEHGEWGSVCDDTWDLEDAHVVCRQLGCGWAVQALPGLHFTPGRGPIH

RDQVNCSGAEAYLWDCPGLPGQHYCGHKEDAGVVCSEHQSWRLTGGADRC

EGQVEVHFRGVWNTVCDSEWYPSEAKVLCQSLGCGTAVERPKGLPHSLSG

RMYYSCNGEELTLSNCSWRFNNSNLCSQSLAARVLCSASRSLHNLSTPEV

PASVQTVTIESSVTVKIENKESR
```

SEQ ID NO: 1 results from the transcription and translation of nucleotide sequences comprising SEQ ID NO.: 2.

```
SEQ ID NO.: 2:
gaccagctca acaccagcag tgcagagagt gagctctggg agccagggga gcggcttccg gtccgtctga caaacgggag cagcagctgc agcgggacgg tggaggtgcg gctcgaggcg tcctgggagc ccgcgtgcgg ggcgctctgg gacagccgcg ccgccgaggc cgtgtgccga gcactgggct gcggcggggc ggaggccgcc tctcagctcg ccccgccgac ccctgagctg ccgccccgc ctgcagccgg aacaccagc gtagcagcta atgccactct ggccggggcg cccgccctcc tgtgcagcgg cgccgagtgg cggctctgcg aggtggtgga gcacgcgtgc cgcagcgacg ggaggcgggc ccgtgtcacc tgtgcagaga accgcgcgct gcgcctggtg gacggtggcg gcgcctgcgc cggccgcgtg gagatgctgg agcatggcga gtggggatca gtgtgcgatg acacttggga cctggaggac gcccacgtgg tgtgcaggca actgggctgc ggctgggcag tccaggcct gcccggcttg cacttcacgc ccggccgcgg gcctatccac cgggaccagg tgaactgctc gggggccgaa gcttacctgt gggactgccc ggggctgcca ggacagcact actgcggcca caaagaggac gcgggcgtgg tgtgctcaga gcaccagtcc tggcgcctga caggggggcgc tgaccgctgc gaggggcagg tggaggtaca cttccgaggg gtctggaaca cagtgtgtga cagtgagtgg tacccatcgg aggccaaggt gctctgccag tccttgggct gtggaactgc ggttgagagg cccaaggggc tgccccactc cttgtccggc aggatgtact actcatgcaa tggggaggag ctcaccctct ccaactgctc ctggcggttc aacaactcca acctctgcag ccagtcgctg gcagccaggg tcctctgctc agcttcccgg agtttgcaca atctgtccac tcccgaagtc cctgcaagtg ttcagacagt cactatagaa tcttctgtga cagtgaaaat agagaacaag gaatctcggt ag
```

As used herein, the expression "pharmaceutically acceptable carrier" means a non-toxic solvent, dispersant, excipient, adjuvant, or other material that is mixed with active ingredient(s) in order to permit the formation of a pharmaceutical composition, i.e., a dosage form capable of administration to the patient. One example of such a carrier is a pharmaceutically acceptable oil typically used for parenteral administration.

The term "pharmaceutically acceptable salts" as used herein means that the salts of the compounds of the present invention can be used in medicinal preparations. Other salts may, however, be useful in the preparation of the compounds according to the invention or of their pharmaceutically acceptable salts.

The term "carrier" refers to a diluent or excipient with which the active ingredient(s) is(are) administered. Such pharmaceutical carriers can be sterile liquids, such as water and oils, including those of petroleum, animal, plant or synthetic origin, such as peanut oil, soybean oil, mineral oil, sesame oil and the like. Water or aqueous solutions of saline solution and aqueous dextrose and glycerol solutions, particularly for injectable solutions, are preferably used as carriers. Suitable pharmaceutical carriers are described in "Remington's Pharmaceutical Sciences" by E. W. Martin, 1995.

An "adjuvant" as used herein is a substance that has few or no pharmacological effects by itself, but may increase the efficacy or potency of other agents when given at (essentially) the same time and oftentimes in (essentially) the same route of administration at (essentially) the same site (e.g. injection into the same muscle) as the other agent. More particularly, when used in the context of immunizations, an adjuvant is a substance that stimulates or that may stimulate the immune system and increase the response to an immunizing agent, without having any specific antigenic effect in itself. More specifically, an immunologic adjuvant can be defined as a substance that acts to accelerate, prolong, or enhance antigen-specific immune responses when used in combination with specific antigen agent(s).

The carriers and the auxiliary substances necessary to manufacture the desired pharmaceutical dosage form of the pharmaceutical composition of the invention will depend, among others factors, on the pharmaceutical dosage form chosen. Said pharmaceutical dosage forms of the pharmaceutical composition of the invention will be manufactured according to conventional methods known by the person skilled in the art.

Examples of pharmaceutical compositions include any solid (tablets, pills, capsules, granulates, etc.) or liquid (solutions, suspensions or emulsions) compositions for oral, topical, intraperitoneal, intravenous or parenteral administration. Furthermore, the pharmaceutical composition can contain, as appropriate, stabilizers, suspensions, preservatives, surfactants and the like.

The skilled in the art will adapt the composition depending on the particular mode of administration. The composition of the present invention may further comprise other therapeutic agents against the infectious diseases or the inflammatory conditions related thereto, or combinations thereof.

Kit-of-Parts

In a second aspect, the present invention provides a kit-of-parts comprising, or alternatively, consisting of, the CD6 product of the present invention, or a derivative thereof, or an isoform thereof, and Imipenem ("the kit-of-parts of the present invention"). The kit-of-parts may also be referred to in the present description as "combination product" and/or "pharmaceutical product", and is defined in the context of the present application as a product or multicomponent system comprising two or more components, which are not necessarily present as a union, e.g., in composition, but which are available for simultaneous, separate or sequential application or administration. Accordingly, the components of the kit-of-parts may be physically separated, in different containers, as it will be described in detail below.

The multicomponent system can be used to store the CD6 product of the present invention, or a derivative thereof, or an isoform thereof, in one container and the Imipenem in the other container. At the appropriate time, the components can be mixed to provide for the composition of the present invention. Alternatively, the components may be used separately or sequentially, namely without being mixed before administration to a subject in need thereof.

In particular, such a kit of parts may comprise or, alternatively, consists of, (a) a first container comprising the CD6 product of the present invention, or a derivative thereof, or an isoform thereof and (b) a second container comprising Imipenem.

The kit-of-parts of the present invention may comprise, or, alternatively, consist of, the CD6 product, or a derivative thereof, or an isoform thereof, and Imipenem as separate entities (e.g., comprised in separate containers), which may be administered to the subject (a mammal, preferably a human) simultaneously, sequentially or separately. In a preferred embodiment, the kit-of-parts of the present invention comprises or, alternatively, consists of, the CD6 product, or a derivative thereof, or an isoform thereof, of the present invention and Imipenem as separate entities (e.g., comprised in separate containers), which may be administered to the subject (a mammal, preferably a human) simultaneously, sequentially or separately. In another embodiment, the containers are combined into a single article of manufacture having a barrier between the containers. This barrier can either be removed or destroyed allowing mixing of the components at the appropriate time.

Accordingly, the present invention provides a kit-of-parts of the present invention simultaneous, separate or sequential use as a medicament, in particular in a therapeutic and/or preventive method of treatment, in a mammal including a human, of an infectious disease, or of an inflammatory condition related to an infectious disease, or of an inflammatory disease related to the presence of a product derived from an infectious agent, as defined below.

The kit-of-parts of the present invention may comprise, or, alternatively, consist of:
a) a pharmaceutical composition comprising the CD6 product, or a derivative thereof, or an isoform thereof, of the present invention and pharmaceutically acceptable carriers, pharmaceutically acceptable salts, adjuvants and/or suitable excipients; and
b) a pharmaceutical composition comprising Imipenem and pharmaceutically acceptable carriers, pharmaceutically acceptable salts, adjuvants and/or suitable excipients.

Both pharmaceutical compositions (a) and (b) are preferably comprised in the kit-of-parts of the present invention as separate entities (e.g., as separate liquid or solid compositions, in separate containers, as described above), which may be administered to the subject (a mammal, preferably a human) simultaneously, sequentially or separately.

As it will be described below, the composition, pharmaceutical composition and/or the kit-of-parts of the present invention may further comprise Cilastatin. Cilastatin may be comprised in the kit-of-parts of the present invention as a (third) separate entity, in a third separate container, preferably in the form of a pharmaceutical composition comprising Cilastatin and pharmaceutically acceptable carriers, pharmaceutically acceptable salts, adjuvants and/or suitable excipients. Preferably, Cilastatin is comprised in the same entity (same container) as Imipenem (e.g., a composition or pharmaceutical composition comprising Imipenem and Cilastatin).

For instance, the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention and Imipenem (or the pharmaceutical composition comprising Imipenem and pharmaceutically acceptable carriers, pharmaceutically acceptable salts, adjuvants and/or suitable excipients) comprised in the kit-of-parts of the present invention, preferably as separate entities, may be administered simultaneously (at the same time) to the subject (a mammal, preferably a human).

Alternatively, the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention and Imipenem (or the pharmaceutical composition comprising Imipenem and pharmaceutically acceptable carriers, pharmaceutically acceptable salts, adjuvants and/or suitable excipients) comprised in the kit-of-parts of the present invention, preferably as separate entities, may be administered sequentially to the subject (a mammal, preferably a human); for instance, the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention may be administered in first place and, afterwards, Imipenem (or the pharmaceutical composition comprising Imipenem and pharmaceutically acceptable carriers, pharmaceutically acceptable salts, adjuvants and/or suitable excipients) is administered to the subject (a mammal, preferably a human).

Preferably, Imipenem (or the pharmaceutical composition comprising Imipenem and pharmaceutically acceptable carriers, pharmaceutically acceptable salts, adjuvants and/or suitable excipients) is first administered to the subject (a mammal, preferably a human) and, afterwards, the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention is administered to the subject.

Alternatively, the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention and Imipenem (or the pharmaceutical composition comprising Imipenem and pharmaceutically acceptable carriers, pharmaceutically acceptable salts, adjuvants and/or suitable excipients) comprised in the kit-of-parts of the present invention, preferably as separate entities, may be administered separately to the subject (a mammal, preferably a human). For example, the subject (a mammal, preferably a human) is already taking Imipenem (or the pharmaceutical composition comprising Imipenem and pharmaceutically acceptable carriers, pharmaceutically acceptable salts, adjuvants and/or suitable excipients) and the CD6 product, or a derivative thereof, or an isoform thereof (or the pharmaceutical composition comprising the CD6 product, or a derivative thereof, or an isoform thereof, and pharmaceutically acceptable carriers, pharmaceutically acceptable salts, adjuvants and/or suitable excipients) of the present invention is administered, preferably in a single dose.

Accordingly, the components of the kit-of-parts of the present invention may be simultaneously, sequentially or separately administered to a subject (a mammal including a human), in a therapeutic and/or preventive method of treatment, preferably, of an infectious disease, or of an inflammatory condition related to an infectious disease, or of an inflammatory disease related to the presence of a product derived from an infectious agent, as it will be described below.

CD6 Product

The CD6 receptor is a 105 to 130 kDa lymphoid-specific surface glycoprotein expressed on the membrane of thymocytes, mature T cells, and the B1a B cell subset, although CD6 expression has also been reported on certain regions of the brain. The CD6 receptor belongs to the SRCR-SF characterized by the presence of one or several repeats of a cysteine-rich extracellular domain named SRCR (cf. M. R. Sarrias et al., "The Scavenger Receptor Cysteine-Rich (SRCR) domain: an ancient and highly conserved protein module of the innate immune system", Crit. Rev. Immunol. 2004, vol. 24, pp. 1-37). Its extracellular region is exclusively composed of three consecutive SRCR domains. Functionally, membrane-bound CD6 is physically associated to the antigen-specific receptor complex present on T (TCR/CD3) cells, where CD6 contributes to either positive or negative modulation of the activation and differentiation signals delivered by that receptor complex. It is well accepted that CD6 binds to its natural ligand ALCAM ("Activated Leukocyte Cell Adhesion Molecule", also known as CD166) (cf. M. A. Bowen et al., "Analysis of domain-domain interactions between CD6 and activated leukocyte cell adhesion molecule (ALCAM)", Tissue Antigens 1996, vol. 48, pp. AS401.32), a broadly expressed adhesion molecule of the Immunoglobulin superfamily.

As used herein, the term "CD6 product" means a product comprising the CD6 ectodomain or a fragment thereof, or an isoform thereof, as described above. Ectodomain refers to the three SRCR domains with the intervening sequences and the stalk region that separates it from the membrane. Suitable CD6 products include natural, synthetic, or recombinant biologically active polypeptide of CD6 ectodomain or fragments thereof; biologically active polypeptide variants of CD6 ectodomain or fragments thereof, including hybrid fusion proteins or homo- or hetero-oligomers. CD6 product is from mammalian origin and more preferably from human origin. Preferably, the CD6 product of the present invention is a recombinant soluble CD6 product (rsCD6). Preferably, the CD6 product of the present invention is a human CD6 product (hCD6). More preferably, the CD6 product of the present invention is a recombinant, soluble, human CD6 product (rshCD6). In another embodiment, the CD6 product is a murine CD6 product (mCD6).

The human full length CD6 protein described in GenBank Accession number NP_006716 has 668 amino acids. The ectodomain is composed of three SRCR domains, the intervening sequences and a stalk region.

In a particular embodiment, the CD6 product (CD6, rsCD6, rshCD6, hCD6 and/or mCD6) of the present invention comprises, or alternatively, consists of, the amino acid sequence SEQ ID NO: 1, as described above. This sequence includes the three SRCR domains, the intervening sequences and the stalk region. As stated above, SEQ ID NO: 1 results from the transcription and translation of nucleotide sequences comprising, or alternatively, consisting of, SEQ ID NO.: 2.

Due to the low plasma levels of soluble CD6, it is not industrially viable to obtain CD6 from purification of plasma or serum. Thus, for the purpose of the invention, it is preferred to produce the CD6 product by genetic engineering methods. Any method commonly used in the art can be employed to produce recombinant soluble CD6, hereafter referred as rsCD6. A preferred method to express and purify rshCD6 is described in the examples of EP 2143436. This method allows to produce rshCD6 for experimental purposes, so industrial scaling-up is necessary to produce large amounts of rshCD6. The CD6 product of the present invention may also be expressed as a fusion protein.

To test whether a CD6 product, or a derivative thereof, or an isoform thereof, is suitable for the purpose of the invention, a microbial binding assay may be used. A suitable assay is described in Example 1 of EP 2143436.

In the description, examples and drawings, rshCD6 refers to the recombinantly soluble obtained human CD6 ectodomain to be distinguished from the membrane-bound CD6 receptor.

Imipenem

Imipenem is a β-lactam antibiotic belonging to the carbapenem class of antibiotics. Carbapenems are highly resistant to the β-lactamase enzymes produced by many multiple drug-resistant G– bacteria. Imipenem acts as an antimicrobial through inhibiting cell wall synthesis of various G+ and G– bacteria, thus reducing the amount of PAMPs released during bacteriolysis. It remains very stable in the presence of β-lactamase (both penicillinase and cephalosporinase) produced by some bacteria, and is a strong inhibitor of β-lactamases from some G– bacteria that are resistant to most β-lactam antibiotics. The systematic IUPAC name for Imipenem is (5R,6S)-6-[(1R)-1-hydroxyethyl]-3-({2-[(iminomethyl)amino]ethyl}thio)-7-oxo-1-azabicyclo[3.2.0]hept-2-ene-2-carboxylic acid, its CAS registry number is 74431-23-5 and its chemical formula is as described below in Formula 1:

Formula 1

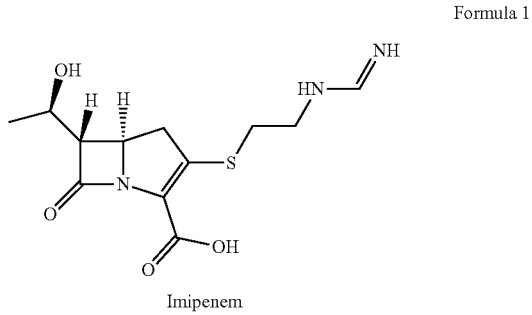 [SMILES: C[C@@H](O)[C@H]1C(=O)N2C(C(=O)O)=C(SCCNC=N)C[C@H]12]

Imipenem

As it will be described in detail below, Imipenem is generally administered together with Cilastatin. Accordingly, in a preferred embodiment, the composition, pharmaceutical composition and/or the kit-of-parts of the present invention further comprises Cilastatin.

Cilastatin

Cilastatin is a compound that inhibits human dehydropeptidase, the enzyme responsible for the in vivo degradation of the antibiotic Imipenem. Accordingly, Cilastatin may be administered together with Imipenem in order to protect its degradation by dehydropeptidase, thereby prolonging the circulation time and thus its antibacterial effect in the body. Cilastatin itself does not have antibiotic activity. As the skilled person is aware of, Imipenem alone is an effective antibiotic and can be administered without cilastatin. However, preferably, Imipenem is administered with cilastatin, preferably in a ratio Imipenem:Cilastatin of 1:1.

Effects of the Composition, Pharmaceutical Composition and Kit-of-Parts of the Invention According to the teaching of the present invention, the composition, pharmaceutical composition and/or the components of the kit-of-parts of the present invention can be administrated to a mammalian, preferably a human. The purpose of the administration of the composition, pharmaceutical composition and/or the components of the kit-of-parts of the present invention may be preventive (to avoid the development of these diseases) and/or therapeutic (to treat these diseases once they have been developed/installed).

It is to be understood that the composition, pharmaceutical composition and/or the components of the kit-of-parts of the present invention are administered in a pharmaceutically acceptable form. Those skilled in the art may ascertain the proper dose using standard procedures. It is understood that the dose should be an effective amount of CD6 product and Imipenem (preferably together with Cilastatin, as described above) in the sense that a reduced inflammatory response is seen in the treated subject.

The present inventors have found that the specific co-administration (simultaneously, sequentially or separately) of a CD6 product and Imipenem (preferably together with Cilastatin, as described above) (intraperitoneal, i.p., and/or intravenous, i.v.) provide for clear improved additive therapeutic effects, particularly in the treatment and/or prevention of an infectious disease, or of an inflammatory condition related to an infectious disease, or of an inflammatory disease related to the presence of a product derived from an infectious agent in a mammal including a human.

It is to be noted that this improved additive effect was not observed when a CD6 product was administered together with other broad-spectra antibiotics of choice for the treatment of an infectious disease, or of an inflammatory condition related to an infectious disease, or of an inflammatory disease related to the presence of a product derived from an infectious agent in a mammal including a human.

For instance, as shown in Example 2 below, non-additive effects were observed when the antibiotic Erythromycin was co-administered with a CD6 product, rshCD6, in CLP-induced sepsis. In addition, as shown in Example 2 below, non-additive effects were observed when the antibiotic Meropenem was co-administered with a CD6 product, rshCD6, in CLP-induced sepsis. CLP-induced sepsis is the gold standard way of inducing experimental sepsis in mice using the cecal ligation and puncture (CLP) method, which causes polymicrobial sepsis.

Both Erythromycin and Meropenem are broad-spectrum antibiotics for the treatment and/or prevention of an infectious disease, or of an inflammatory condition related to an infectious disease, such as sepsis.

Meropenem is a broad-spectrum bactericidal injectable antibiotic that is generally used to treat a wide variety of infections. It is a β-lactam and belongs to the subgroup of carbapenem, similar to Imipenem. Meropenem is, however, non-degraded by the human enzyme dehydropeptidase, making unnecessary its association with Cilastatin. The systematic IUPAC name of Meropenem is (4R,5S,6S)-3-(((3S,5S)-5-(Dimethylcarbamoyl)pyrrolidin-3-yl)thio)-6-((R)-1-hydroxyethyl)-4-methyl-7-oxo-1-azabicyclo[3.2.0]hept-2-ene-2-carboxylic acid, its CAS registry number is 119478-56-7 and its chemical formula is as represented below in Formula 2:

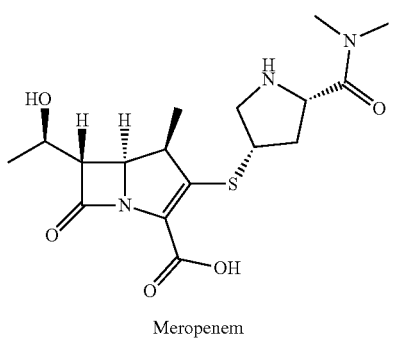

Meropenem

Erythromycin is a bacteriostatic antibiotic effective against systemic infections caused by both G+ and G− bacterial species from different origins (mainly, skin, and respiratory tract). The systematic IUPAC name of Erythromycin is (3R,4S,5S,6R,7R,9R,11R,12R,13S,14R)-6-{[(2S,3R,4S,6R)-4-(dimethylamino)-3-hydroxy-6-methyloxan-2-yl]oxy}-14-ethyl-7,12,13-trihydroxy-4-{[(2R,4R,5S,6S)-5-hydroxy-4-methoxy-4,6-dimethyloxan-2-yl]oxy}-3,5,7,9,11,13-hexamethyl-1-oxacyclotetradecane-2,10-dione. Erythromycin inhibits protein synthesis and growth of bacteria by interfering with aminoacyl translocation, preventing the transfer of the tRNA bound at the A site of the rRNA complex to the P site of the rRNA complex.

Methods of Treatment

In a further aspect, the composition, pharmaceutical composition and/or the kit-of-parts of the present invention, in any of their variants, can be used as a medicament, preferably in a therapeutic and/or preventive method of treatment, in a mammal including a human, of an infectious disease, or of an inflammatory condition related to an infectious disease, or of an inflammatory disease related to the presence of a product derived from an infectious agent. The present invention thus provides a therapeutic and/or preventive method of treatment of an infectious disease, or of an inflammatory condition related to an infectious disease, or of an inflammatory disease related to the presence of a product derived from an infectious agent comprising the administration of the composition, pharmaceutical composition and/or of the components of the kit-of-parts of the present invention to a mammal. In a preferred embodiment, the mammal is a human.

For instance, the present invention provides the kit-of-parts of the present invention for simultaneous, sequential or separate use as a medicament. In particular, the present invention provides the kit-of-parts of the present invention for simultaneous, sequential or separate use in a therapeutic and/or preventive method of treatment, in a mammal including a human, of an infectious disease, or of an inflammatory condition related to an infectious disease, or of an inflammatory disease related to the presence of a product derived from an infectious agent.

In a particular embodiment of the invention, the infectious disease is a microbial infection. In more particular embodiments, the microbial infection is selected from the group consisting of a bacterial infection (either G+ or G− bacteria, saprophytic or pathogenic, aerobic or anaerobic), a fungal infection, a viral infection, a parasitic infection, and combinations thereof (polymicrobial infection).

In another particular embodiment, the infectious disease is a septicemia. As used herein, the term "septicemia" refers to the presence of any microbe in blood stream. Particularly, the septicemia is selected from the group consisting of a bacteremia, a fungemia, a viremia, a parasitemia, and combinations thereof.

The presence of viable microbes is found in most cases of inflammatory conditions related to an infectious disease, whereas 20% to 30% of patients do not have microbes identified from any source but products derived from them. Thus, in another embodiment, the inflammatory condition is related to a product derived from an infectious agent. Particularly, the infectious agent is selected from the group consisting of a bacterium (either G+ or G− bacteria, saprophytic or pathogenic, aerobic or anaerobic), a fungus, a virus, a parasite, and/or combinations thereof.

Sepsis is defined as the presence or presumed presence of an infection accompanied by evidence of a systemic response called the systemic inflammatory response syndrome (SIRS). For sepsis definition, reference is made to the article "Severe sepsis and septic shock: review of the literature and emergency department management guidelines", H. B. Nguyen et al., Ann. Emergency Med. 2006, vol. 48, pp. 28-54. Sepsis is usually caused by bacterial infections (either G+ or G− bacteria) but can also be caused by other pathogens. Most often however, sepsis is caused by G+ and G− bacterial infections. However, the injury and symptoms attributable to sepsis are not only caused by the whole alive bacteria but are also caused by a component of the bacteria cell wall known as endotoxins. Endotoxins (e.g., LPS, LTA, PGN) are glycolipids that are ubiquitous in the outer membrane of G+ and G− bacteria. Endotoxins are released when the immune system destroys the invading bacteria. The released endotoxins bind to immune cells (monocytes, macrophages, granulocytes, lymphocytes, and endothelial and epithelial cells) and trigger the production of various soluble mediators of inflammation such as cytokines (e.g., TNF-α, IL-1β, and IL-6) and chemokines (e.g., IL-8), which are a major cause of severe forms of sepsis.

In a particular embodiment of the invention, the inflammatory condition is SIRS (systemic inflammatory response syndrome). In another particular embodiment, the inflammatory condition is sepsis. SIRS is defined as the presence of two or more of the following: (1) temperature greater than 38° C. or less than 36° C.; (2) pulse rate greater than 90 beats/min; (3) respiratory rate greater than 20 breaths/min (or PCO2 less than 32 torr); and (4) white blood cells count greater than 12000/mm<3> or less than 4000/mm<3>, or greater than 10% immature band forms.

In a particular embodiment, the sepsis is polymicrobial sepsis. Polymicrobial sepsis is defined as a complex systemic infection involving concurrence of multiple infectious agents (e.g., bacterial and fungal; saprophytic and pathogenous; aerobic and anaerobic, etc.).

In another particular embodiment, the inflammatory condition is severe sepsis. Severe sepsis is defined as the sepsis which is accompanied by one or more organ dysfunctions. Organ dysfunction can be defined as acute lung injury; coagulation abnormalities; thrombocytopenia; altered mental status; renal, liver, or cardiac failure; or hypoperfusion with lactic acidosis.

In another particular embodiment, the inflammatory condition is septic shock. Septic shock is defined as the presence of sepsis and refractory hypotension, i.e., systolic blood pressure less than 90 mmHg, mean arterial pressure less than 65 mmHg, or a decrease of 40 mmHg in systolic blood pressure compared to baseline unresponsive to a crystalloid fluid challenge of 20 to 40 ml/kg. Thus, septic shock is effectively a form of severe sepsis. Finally, the septic shock may be endotoxin-induced septic shock.

The source of the infection can be any of a number of places throughout the body. Common sites of infection that can lead to sepsis comprise the following:

Inflammation of the appendix (appendicitis), diverticulitis, bowel problems, infection of the abdominal cavity (peritonitis), and gallbladder or liver infections; inflammation or infections of the brain or the spinal cord (meningitis, encephalitis); lung infections such as pneumonia; skin infections through wounds or through openings made with intravenous catheters, cellulitis (inflammation of the skin's connective tissue); urinary tract infections, especially if the patient has a urinary catheter to drain urine; dental and gynecological examinations or treatments; blunt or penetrating trauma, surgery, and endocarditis.

The administration of the composition, pharmaceutical composition and/or or the components of the kit-of-parts of the present invention, in any of their variants, to a mammal, including a human, may be done intraperitoneally (i.p.) and/or intravenously (i.v.). In a preferred embodiment, the composition, pharmaceutical composition and/or the product of the present invention are administered to a mammal, including a human, intravenously. The present inventors have found that the use of the i.v. route allowed extending the therapeutic effects of rshCD6 up to +3 h or +6 h post-CLP induction (see Examples below).

Preferably, the components of the kit-of-parts of the present invention are administered as follows. A single dose of the CD6 product, or a derivative thereof, or an isoform thereof, preferably rshCD6 (or a pharmaceutical composition comprising the CD6 product, preferably rshCD6, or a derivative thereof, or an isoform thereof, and pharmaceutically acceptable carriers, pharmaceutically acceptable salts, adjuvants and/or suitable excipients) is administered as early as possible, preferably i.v., during Imipenem treatment (preferably together with Cilastatin, as described above). The optimal rshCD6 dose in mice is 1.25-2.50 mg/kg. As the skilled person would understand, the optimal rshCD6 dose for other mammals, including humans, should be established in clinical assays.

In another preferred embodiment, the components of the kit-of-parts of the present invention are administered as follows. A single dose of the CD6 product, or a derivative thereof, or an isoform thereof, preferably rshCD6 (or a pharmaceutical composition comprising the CD6 product, preferably rshCD6, or a derivative thereof, or an isoform thereof, and pharmaceutically acceptable carriers, pharmaceutically acceptable salts, adjuvants and/or suitable excipients) is administered as early as possible, preferably i.v., and, subsequently, Imipenem (or a pharmaceutical composition comprising Imipenem and pharmaceutically acceptable carriers, pharmaceutically acceptable salts, adjuvants and/or suitable excipients) (preferably together with Cilastatin, as described above) is administered to a subject in need thereof.

In another preferred embodiment, the components of the kit-of-parts of the present invention are administered as follows. First, Imipenem (or a pharmaceutical composition comprising Imipenem and pharmaceutically acceptable carriers, pharmaceutically acceptable salts, adjuvants and/or suitable excipients) (preferably together with Cilastatin, as described above) is administered to a subject in need thereof. Subsequently, a single dose of the CD6 product, or a derivative thereof, or an isoform thereof, preferably rshCD6 (or a pharmaceutical composition comprising the CD6 product, preferably rshCD6, or a derivative thereof, or an isoform thereof, and pharmaceutically acceptable carriers, pharmaceutically acceptable salts, adjuvants and/or suitable excipients) is administered, preferably i.v.

Alternatively, not only a single dose of CD6 product of the present invention, as described above, is administered to a subject in need thereof, but more than one dose may be administered, such as two, three, four, five, six, seven, eight, nine, ten or more doses may be administered to a subject in need thereof. As the skilled person may understand, one two, three, four, five, six, seven, eight, nine, ten or more doses may be administered either before, during or after the administration of Imipenem (preferably together with Cilastatin). In addition, the CD6 product may not be administered in doses, but as continuous perfusion (preferably i.v.), either before, during or after the administration of Imipenem (preferably together with Cilastatin).

Of course, the subject in need thereof may be under the treatment of other drugs such as other antibiotics when the composition, pharmaceutical composition and/or components of the kit-of-parts of the present invention, in any of its variants, are administered.

The present invention further provides a CD6 product, or a derivative thereof, for use in a therapeutic and/or preventive method of treatment, in a mammal including a human, of an infectious disease, or of an inflammatory condition related to an infectious disease, or of an inflammatory disease related to the presence of a product derived from an infectious agent, wherein the method comprises simultaneously, sequentially or separately administering to a mammal including a human the CD6 product, or a derivative thereof and Imipenem. Preferably, the method further comprises the administration of Cilastatin.

In addition, the present invention provides Imipenem, preferably together with Cilastatin, for use in a therapeutic and/or preventive method of treatment, in a mammal including a human, of an infectious disease, or of an inflammatory condition related to an infectious disease, or of an inflammatory disease related to the presence of a product derived from an infectious agent, wherein the method comprises simultaneously, sequentially or separately administering to a mammal including a human Imipenem and a CD6 product, or a derivative thereof. Preferably, the method further comprises the administration of Cilastatin.

Accordingly, a therapeutically effective amount of the CD6 product, or a derivative thereof, or an isoform thereof (or a pharmaceutical composition comprising the CD6 product, preferably rshCD6, or a derivative thereof, or an isoform thereof, and pharmaceutically acceptable carriers, pharmaceutically acceptable salts, adjuvants and/or suitable excipients), and of Imipenem (or a pharmaceutical composition comprising Imipenem and pharmaceutically acceptable carriers, pharmaceutically acceptable salts, adjuvants and/or suitable excipients) (preferably together with Cilastatin, as stated above) may be administered sequentially or separately to a subject (a mammal, including a human) in need thereof. This is particularly the case when the subject is already under antibiotic treatment with Imipenem (preferably together with Cilastatin) and sometime later, a therapeutically effective amount of the CD6 product, or a derivative thereof is administered to the subject.

Preferably, a therapeutically effective amount of the CD6 product, or a derivative thereof, or an isoform thereof (or a pharmaceutical composition comprising the CD6 product, preferably rshCD6, or a derivative thereof, or an isoform thereof, and pharmaceutically acceptable carriers, pharmaceutically acceptable salts, adjuvants and/or suitable excipients), and of Imipenem (or a pharmaceutical composition comprising Imipenem and pharmaceutically acceptable carriers, pharmaceutically acceptable salts, adjuvants and/or suitable excipients) (preferably together with Cilastatin, as stated above) are administered simultaneously to a subject (a mammal, including a human) in need thereof. For instance, a subject with clinical symptoms of infection may be subjected to treatment with antibiotics. If the infection does not remit, the clinician may administer the composition, pharmaceutical composition and/or the components of the kit-of-parts of the present invention as described above.

In a preferred embodiment, the CD6 product of the present invention, or a derivative thereof, or an isoform thereof is administered to the subject in need thereof through gene therapy. For instance, sustained CD6 levels in plasma may be achieved through adenovirus-mediated expression (e.g., liver-specific AAV-mediated expression). This is particularly suitable for immunodeficient subjects (patients), such as paediatric or adult immunodeficient subjects (patients). These subjects (patients) would already be treated with the CD6 product, or derivative thereof, or isoform thereof. Once there are clinical manifestations of an infectious disease, or of an inflammatory condition related to an infectious disease, or of an inflammatory disease related to the presence of a product derived from an infectious agent, as described above, Imipenem (or a pharmaceutical composition comprising Imipenem and pharmaceutically acceptable carriers, pharmaceutically acceptable salts, adjuvants and/or suitable excipients) (preferably together with Cilastatin, as stated above) is administered to the subject (patient).

"Therapeutically effective amount" means an amount of the compound which is effective in treating the named disorder or condition.

As used herein, the term "about" means the indicated value ±1% of its value, or the term "about" means the indicated value ±2% of its value, or the term "about" means the indicated value ±5% of its value, the term "about" means the indicated value ±10% of its value, or the term "about" means the indicated value ±20% of its value, or the term "about" means the indicated value ±30% of its value; preferably the term "about" means exactly the indicated value (±0%).

The terms "treatment" or "therapy" encompass both prophylactic and curative methods of treating disease, since both are directed to the maintenance or restoration of health. Irrespective of the origin of pain, discomfort or incapacity, its relief, by the administration of an appropriate agent, is to be construed as therapy or therapeutic use in the context of the present application.

The composition, pharmaceutical composition and/or kit-of-parts of the invention may thus be used in a method of therapeutic treatment (after the clinical manifestation of the disease) and/or prophylactic treatment (before the clinical manifestation of the disease).

During the description of the claims, the word "comprising" and its variants does not intend to exclude other technical characteristics, additives, components or steps. In addition, the term "comprising" may also encompass the term "consisting of".

Unless otherwise defined, all technical and scientific terms used herein have the same meaning as commonly understood by one of ordinary skilled in the art to which this invention belongs. Methods and materials similar or equivalent to those described herein can be used in the practice of the present invention. Additional objects, advantages and features of the invention will become apparent to those skilled in the art upon examination of the description or may be learned by practice of the invention. The following examples and drawings are provided by way of illustration, and they are not intended to be limiting of the present invention.

EXAMPLES

Materials and Methods
Expression, Purification and Biotinylation of Recombinant Proteins Production of purified rshCD6 and rshCD5 proteins (in PBS with 10% glycerol, pH 7.4) was done by using SURE CHO-M Cell Line™ clones from the Selexis SUREtechnology Platform™ (Geneva, Switzerland) and subjecting serum-free supernatants to size-exclusion chromatography protocols developed at PX'Therapeutics (Grenoble, France).

Cecal Ligation and Puncture (CLP) Procedure

All animal procedures were approved by the Animal Experimentation Ethical Committee, University of Barcelona. CLP-induced septic shock was induced in 8-10 week old C57BL/6J male mice (20-25 g; Charles River) following previously reported methods (Rittirsch D, et al., 2009. Immunodesign of experimental sepsis by cecal ligation and puncture. Nat Protoc 4:31-36). The severity of the CLP model was adjusted to achieve a high-grade mortality (meaning ≥90% mortality in the first 48-72 h) by ligating 75% of cecum. Mice were anesthetized with 100 mg/kg ketamine (Imalgéne 1000, Merial) and 10 mg/kg xylazine (Rompun, Bayer) subsequently resuscitated with 1 mL saline serum intraperitoneally (i.p.). To mitigate pain effects, 0.05 mg/kg/12 h Buprenorphin was administered subcutaneously. When indicated Imipenem/Cilastatin (33 mg/kg/8 h; Actavis, Iceland), Erythromycin (2.75 µg/kg/8 h), Meropenem (17 mg/kg/8 h) and/or a single dose of rshCD6 (0.32-2.5 mg/kg) were administered via i.p. or i.v. The final experimental outcome was observation of spontaneous mortality, which was represented as percentage of surviving animals along time. Daily weight loss monitoring (usually was of 10-15% in the first 48 h post-CLP) allowed exclusion of animals not undergoing clinical sepsis.

Determination of Bacterial Load

Blood samples were taken from live mice by facial vein puncture at 4 h post-CLP. Peritoneal, spleen and kidney samples were obtained from euthanized mice at 20 h post-CLP. For peritoneal lavage, euthanized mice were i.p. infused with 3 mL cold PBS. After gently abdominal massaging for 5 min, the peritoneal fluid was collected taking care to avoid clogging by the fat tissue and not to damage internal organs. Blood-contaminated peritoneal samples were discarded. The collected peritoneal fluid was centrifuged (3500 rpm, 10 min at 4° C.) and the pellet resuspended in 200 µL PBS. Spleen (100 mg) and kidney (250 mg) homogenization was performed by pressing the organs with a syringe plunger through a 40 µm cell strainer in 3 mL cold PBS. The resulting homogenates were centrifuged (3500 rpm, 10 min at 4° C.) and pellets resuspended in 750 µL PBS. Serial dilutions of blood, peritoneal lavage, and spleen and kidney homogenates were prepared in sterile PBS for plating on agar with 5% sheep blood (Becton Dikinson, UK) at 37° C. overnight. Viable bacterial counts were expressed as colony-forming units (cfu) per mL or mg.

ELISA Measurement of rshCD6 and Cytokine Plasma Levels

Plasma levels of rshCD6 were determined by sandwich ELISA, using unlabelled (161.8) and biotin-labelled (SPV-L14.2) anti-CD6 monoclonal antibodies (2 µg/mL, each) as capture and detection antisera, respectively. Serial dilutions of purified rshCD6 were used as a standard. Diluted or undiluted plasma samples were used for monitoring IL-6 (1:70; Mouse IL-6 ELISA Set, BD Bioscience-555240), TNF-α (1:10; Mouse TNF-α ELISA Set, BD Bioscience-558534), IL-10 (neat; Mouse IL-10 ELISA Set, BD Bioscience-555252), and IL-1β (neat; Mouse IL-1β ELISA Set, BD Bioscience-559603) levels by commercially available ELISA kits, following manufacturer's instructions. Plates were developed with horseradish peroxidase-labeled streptavidin (Roche Diagnostics) and TMB Substrate Reagent Set (BD OptEIA, BD Biosciences), and further measurement of optical density at 450 nm (OD450 nm).

Recombinant AAV Vectors Construction and Virus Production and Purification

Recombinant AAV8 vectors expressing mouse soluble CD6 (msCD6) or luciferase protein under the control of the chimerical liver-specific promoter formed by the albumin enhancer and human α-1-antitrypsin promoter (EalbAAT) were constructed (Vanrell L, et al., 2011. Development of a liver-specific Tet-on inducible system for AAV vectors and its application in the treatment of liver cancer. Mol Ther 19:1245-1253). The cDNA coding for signal peptide from Immunglobulin κ light chain variable region fused in frame with amino acids Gly25-Thr398 from msCD6 (Whitney G, et al., 1995. Cloning and characterization of murine CD6. Mol Immunol 32:89-92) was cloned as Sal I-Not I into AAV2 genome obtaining the plasmid pAAV-EalbAAT-rmsCD6. For AAV-rmsCD6 virus production, a mixture of pAAV-EalbAAT-rmsCD6 (20 µg) and pDP8.ape (55 µg; PlasmidFactory GmbH & Co. KG, Bielefeld Germany) plasmids was transfected into 15-cm plates seeded with semi-confluent 293 T cells using linear polyethylenimine (PEI, MW 25 kDa; Polysciences, Warrington, Pa.). Cells were harvested 72 h post-transfection and virus released by three rounds of cell freeze-thawing. Crude lysates were treated with Benzonase (50 U/mL) for 1 h at 37° C. and kept at −80° C. until purification by using iodixanol gradients according to a previously described method (Zolotukhin S, et al., 1999. Recombinant adeno-associated virus purification using novel methods improves infectious titer and yield. Gene Ther 6:973-985). The purified viral batches were concentrated by cross-flow filtration and then filtered (0.22 µm) and stored at 80° C. Viral titres (in terms of genome copies per mL) were determined by real-time quantitative PCR using primers specific to the human α-1-antitrypsin promoter (AAT-Forward (Fw): 5'-CCCTGTTTGC-TCCTCCGATAA-3' (SEQ ID NO: 3) and AAT-Reverse (Rv): 5'-GTCCGTATTTAAGCAGTGGATCCA-3' (SEQ ID NO: 4)). For AAV biodistribution studies, mice received a single i.v. dose of 1×10$^{11}$ viral particles/mouse (200 µL final volume), and msCD6 plasma levels were monitored by ELISA (DuoSet mouse CD6, R&D Systems) at different time points.

Statistical Analysis

Statistical analyses were performed using the Prism 5.00 computer program (GraphPad Software Inc, San Diego, Calif.). The survival data were represented in Kaplan-Meier graphs and analysed by the Log-Rank $\chi^2$ test. Statistical significant differences (P<0.01) were determined by 2-tailed non parametric Mann-Whitney test.

Results

Example 1. Protective Effects of Human and Mouse Soluble Scavenger-Like CD6 Lymphocyte Receptor in a Lethal Model of Polymicrobial Sepsis Prophylactic Effects of i.p. rshCD6 Infusion in CLP-Induced Septic Shock Given the reported ability of rshCD6 for targeting pathogenic factors from G+ (LTA, PGN) and G− (LPS) bacteria (Sarrias M-R, et al., 2007. CD6 binds to pathogen-associated molecular patterns and protects from LPS-induced septic shock. Proc Natl Acad Sci USA 104:11724-1197; Florensa M, et al., 2014. Targeting of key pathogenic factors from gram-positive bacteria by the soluble ectodomain of the scavenger-like lymphocyte receptor CD6. J Infect Dis 209: 1077-1086), its potential use for prevention and/or treatment of polymicrobial sepsis of intra-abdominal origin, namely CLP, was tested. Based on previous results obtained in a mouse model of monobacterial-induced peritonitis (Florensa M, et al., 2014. Targeting of key pathogenic factors from gram-positive bacteria by the soluble ectodomain of the scavenger-like lymphocyte receptor CD6. J Infect Dis 209: 1077-1086) C57BL/6 mice were first infused via i.p. with a single dose of rshCD6 (1.25 mg/kg) 1 h before (−1 h) CLP induction. As illustrated by FIG. 1A, survival was significantly increased (P=0.0067) for mice treated with rshCD6 (47.06%, n=15) in comparison to the saline-treated group (6.52%, n=18) or with rshCD5 (11.11%, n=9). These prophylactic effects on mouse survival were dose-dependent, with doses above 0.625 mg/kg giving statistical significant results and reaching maximal efficacy at 2.5 mg/kg (FIG. 1B). Prophylactic infusion of rshCD6 also significantly lowered plasma levels of the pro-inflammatory cytokines IL-1β, IL-6 and TNF-α together with higher levels of anti-inflammatory cytokine IL-10, compared to the saline-treated group (FIG. 1C). Similarly, bacterial load from blood, spleen and kidney samples was also lowered by prophylactic infusion of rshCD6 compared to the saline-treated group (FIG. 1D), reaching statistical significance for blood and kidney at 4 and 20 h, respectively. Taken together, these results indicate that prophylactic infusion of rshCD6 has specific and dose-dependent effects on mouse survival post CLP-induced septic shock, showing also significant reductions on systemic inflammation and bacterial load parameters.

Therapeutic Effects of i.p. rshCD6 Infusion in CLP-Induced Septic Shock

Figure 2:
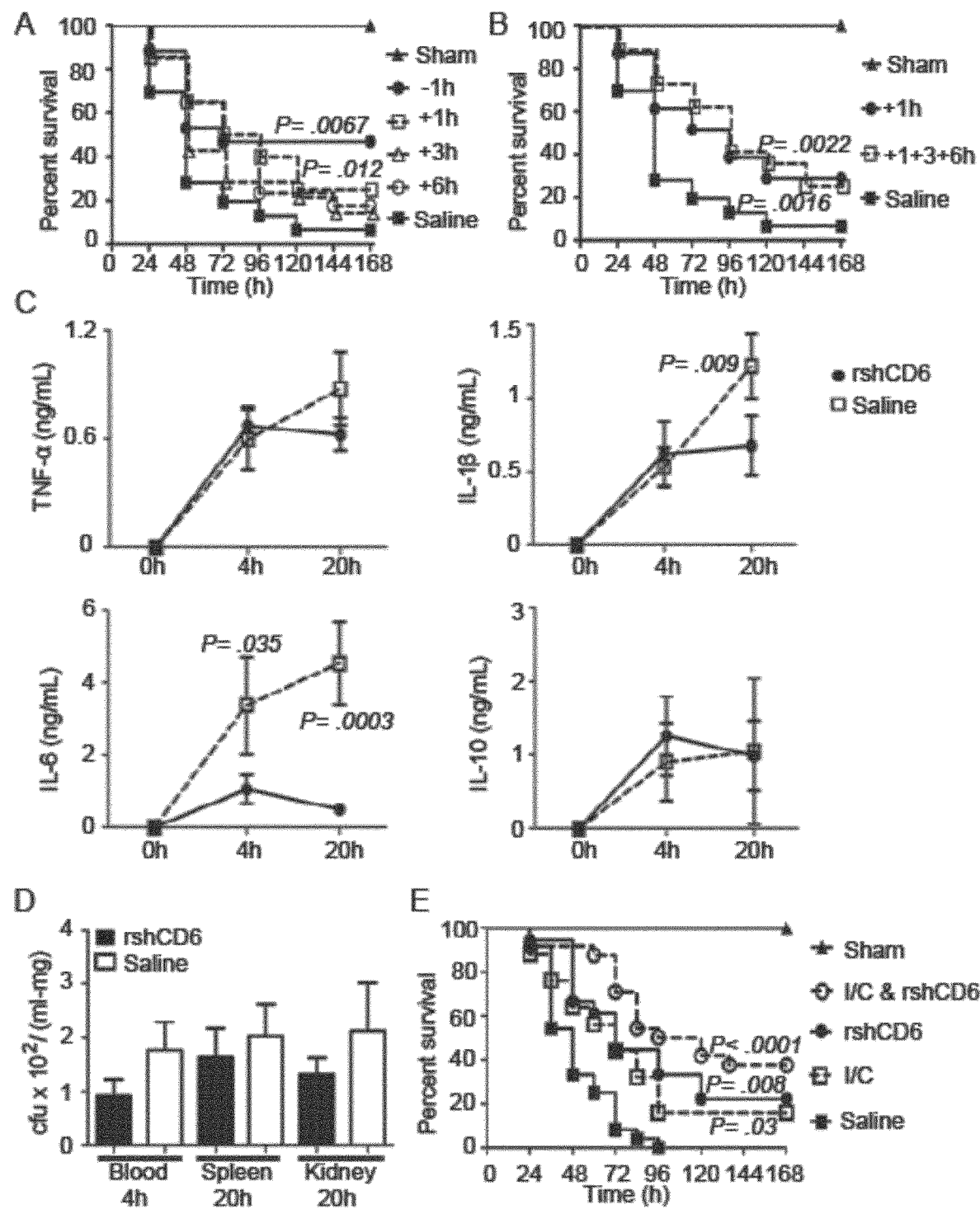
FIG. 2. Effect of therapeutic i.p. rshCD6 infusion on CLP-induced polymicrobial septic shock. A, C57BL/6J mice were infused i.p. with either saline (n=46) or rshCD6 (1.25 mg/kg) at different time points either before (−1 h; n=19) or after (+1 h, n=31; +3 h, n=14; +6 h, n=17) of CLP-induced septic shock. B, C57BL/6J were i.p. infused with a single dose of saline (n=46) or rshCD6 (1.25 mg/kg) 1 h post-CLP (+1 h, n=31) or a repeated dosage of rshCD6 (1.25 mg/kg) at +1 h, +3 h, and +6 h (1+3+6 h; n=19) post CLP-induced septic shock. In A and B average percent survival was analyzed over time, and statistical comparisons made by using the long-rank t-test. C, Plasma levels of pro- (TNF-α, IL-1β, IL-6) and anti- (IL-10) inflammatory cytokines were monitored by ELISA at the indicated time points (+4 h, +20 h) post CLP-induced septic shock in C57BL/6J mice therapeutically treated (+1 h) via i.p. with either saline (n=10) or rshCD6 (1.25 mg/kg; n=10). Data are expressed as ng or pg/mL (mean±SD), and statistical comparisons made by using the 2-tailed Student t-test. D, Bacterial load was monitored in blood, spleen and kidney at the indicated time points (+4 h, +20 h) post CLP-induced septic shock in C57BL/6J mice therapeutically treated (+1 h) with either saline (n=10) or rshCD6 (1.25 mg/kg; n=10). Data are expressed as cfu×$10^2$/mL or mg (mean±SD), and statistical comparisons made using the 2-tailed Student t-test. E, C57BL/6J were therapeutically (+1 h) infused via i.p. with saline (n=24), rshCD6 (1.25 mg/kg n=18), Imipenem/Cilastatin (I/C, 33 mg/kg/8 h; n=25) or a combination of the later (n=24) and percent average of mouse survival represented over time.

To further explore the putative therapeutic effects of rshCD6 infusion, time-course experiments were performed. As illustrated by FIG. 2A, a single infusion of rshCD6 (1.25 mg/kg) via i.p. at different times pre- and post-CLP, showed statistical significant effects (P=0.012) on mouse survival when administered at +1 h (29.03%, n=31) but not +3 h (14.28%, n=14) or +6 h (17.65%, n=17) post-CLP, compared to the saline-treated group (6.52%, n=46). The survival achieved by infusing rshCD6 at +1 h was however lower than that obtained at −1 h pre-CLP, and was not improved by repeated dosage at +1 h, +3 h and +6 h post-CLP (26.32%, n=19), although the latter still reached statistical significance (P=0.0016) compared with the saline-treated group (FIG. 2B). Monitoring of cytokine plasma levels at 4 and 20 h post-CLP showed that the mice treated with rshCD6 via i.p. +1 h post-CLP presented lower pro-inflammatory cytokine levels, which reached statistical significance for IL-1β and IL-6, but not TNF-α, with no differences observed for the anti-inflammatory cytokine IL-10, compared with the saline-treated group (FIG. 2C). Similarly, monitoring of bacterial load showed lower cfu from blood, spleen and kidney of mice treated with rshCD6 at +1 h post-CLP, which did not reached statistical significance with regard to the saline-treated group (FIG. 2D). In conclusion, these results indicate that therapeutic effects of rshCD6 infusion via i.p. route are only achieved at early (+1 h) but not at later (+3 h or +6 h) time points post-CLP induction, even when administered as repeated dosage.

Therapeutic Effects of i.v. rshCD6 Infusion in CLP-Induced Septic Shock

Figure 3:
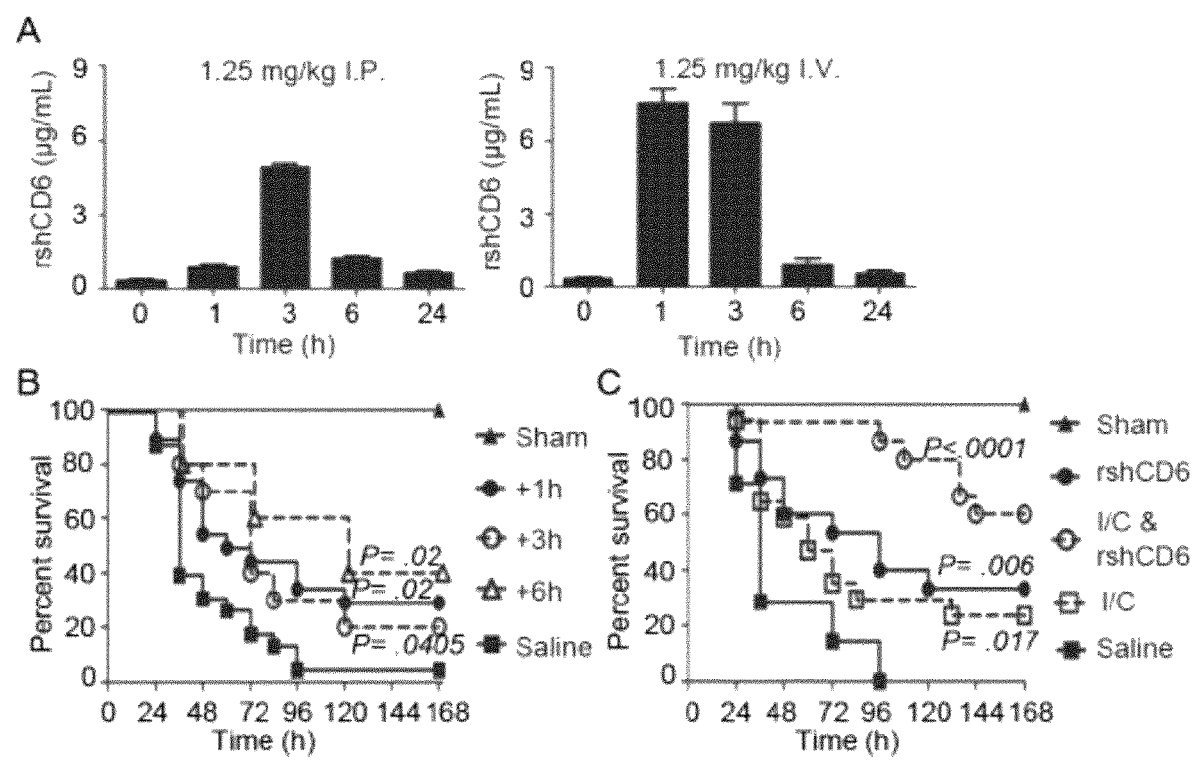
FIG. 3. Effects of therapeutic i.v. rshCD6 infusion on CLP-induced polymicrobial septic shock. A, C57BL/6J mice were infused via i.p. (n=6, left) or i.v. (intravenous) (n=6, right) with rshCD6 (1.25 mg/kg) and plasma levels of rshCD6 determined by ELISA as μg/mL (mean±SD). B, C57BL/6J were infused via i.v. with saline (n=18) or rshCD6 (1.25 mg/kg) at different time points (+1 h, n=20; +3 h, n=10; and +6 h, n=5) post CLP-induced septic shock. C, C57BL/6J mice were therapeutically (+1 h) infused via i.v. with saline (n=24), rshCD6 (1.25 mg/kg, n=18), Imipenem/Cilastatin (I/C, 33 mg/kg/8 h; n=25) or a combination of the two later (n=24). In B and C, average survival was analyzed over time for each group and statistically compared to the saline-treated group using the long-rank t-test.

The i.p. route is widely used for the systemic administration of compounds to animals (Lukas G, et al., 1971. The route of absorption of intraperitoneally administered compounds. J Pharmacol Exp Ther 178:562-4), though the route of choice for human clinical purposes is the i.v. one, a matter that can influence systemic drug bioavailability. Accordingly, rshCD6 plasma levels differed when a single dose (1.25 mg/kg) was administered to C57BL/6 mice either via i.p. or i.v. As illustrated by FIG. 3A, maximal rshCD6 levels were achieved at +3 h post i.p. infusion, and then decreased to nearly basal levels by +6 h. By contrast, i.v. infusion achieved maximal and sustained plasma levels at +1 h-+3 h, which then declined to nearly basal levels by +6 h. Interestingly, maximal levels achieved via i.v. were higher than those obtained via i.p., thus supporting a higher and more sustained systemic bioavailability for the i.v. route.

In light of these results, time-course experiments exploring the therapeutic efficacy of i.v. rshCD6 infusion on CLP-induced mouse survival were performed. As shown in FIG. 3B, mouse survival was significantly improved compared with the saline-treated group by a single dose of i.v. rshCD6 (1.25 mg/kg) at +1 h (30%, n=20, P=0.02), but also at +3 h (20%, n=10; P=0.0405) and +6 h (40%, n=5; P=0.02) post-CLP. Although there were not statistical significant differences between rshCD6-treated groups at +1 h, +3 h and +6 h, the results indicate that the i.v. route extends the therapeutic effects of rshCD6 over time.

Figure 4:
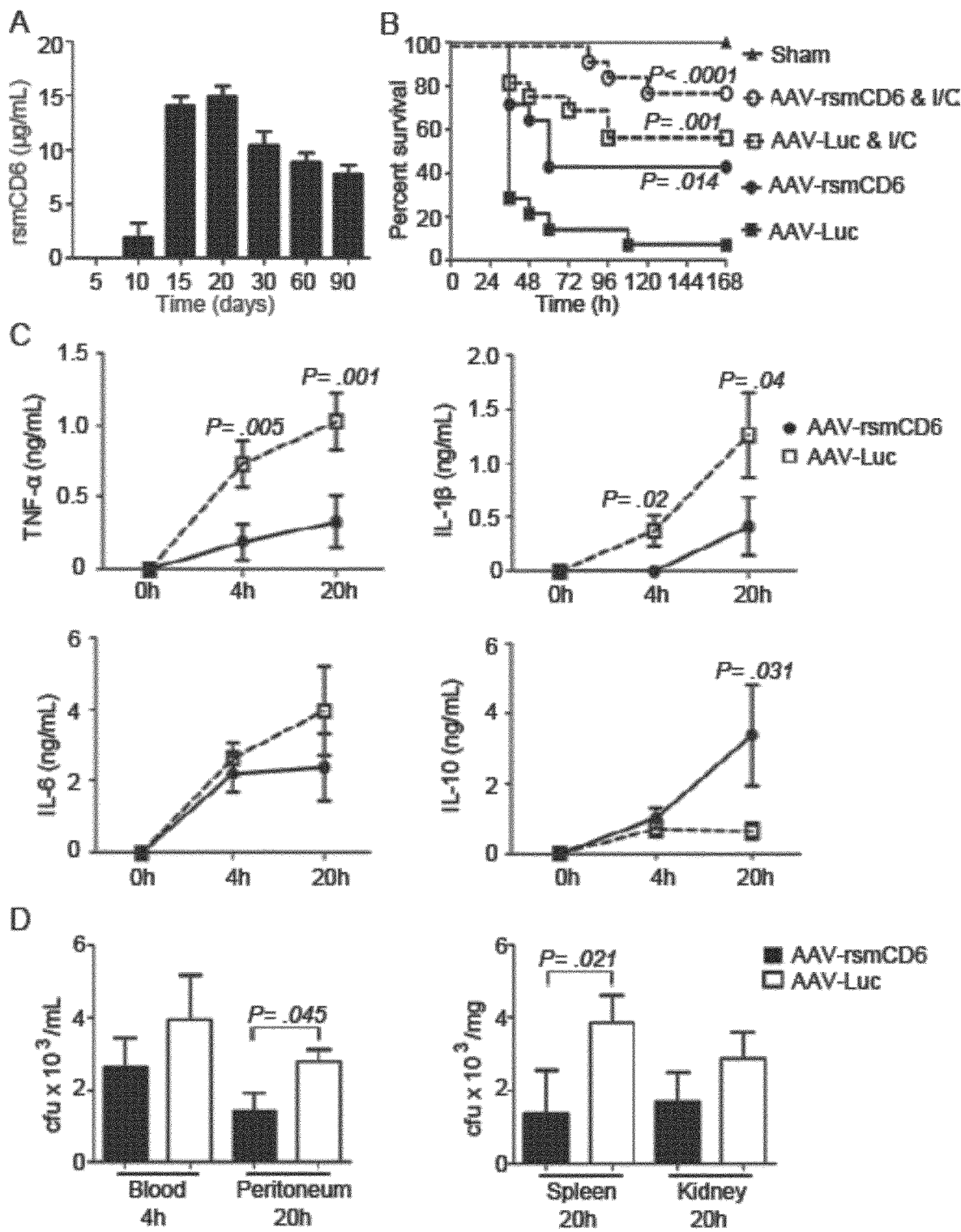
FIG. 4. Effect of AAV-mediated gene delivery of rsmCD6 on CLP-induced polymicrobial septic shock. A, C57BL/6J mice (n=6) were treated via i.v. with hepato-tropic AAV virus (adeno-associated virus) coding for rsmCD6 (AAV-rsmCD6) and bled at different time points for monitoring rsmCD6 plasma levels by ELISA. Data are expressed as μg/mL (mean±SD). B, C57BL/6J mice i.v. treated with 1×$10^{11}$ AAV-rsmCD6 or AAV-Luc viral particles two weeks before CLP-induced septic shock were therapeutically (+1 h) infused via i.p. with (n=15 and n=16, respectively) or without (n=14 and n=13, respectively) Imipenem/Cilastatin (I/C, 33 mg/kg/8 h). Average percent survival was analyzed over time, and statistical comparisons made by using the long-rank t-test. C, Plasma levels of the indicated cytokines were monitored by ELISA at the indicated time points (+4 h, +20 h) post CLP-induced septic shock in C57BL/6J mice treated two weeks before with 1×$10^{11}$ AAV-rsmCD6 (n=10) or AAV-Luc (n=10) viral particle. Data are expressed as ng or pg/mL (mean±SD), and statistical comparisons made using the 2-tailed Student t-test. D, Bacterial load was monitored at the indicated time points (+4 h, +20 h) post CLP-induction in blood, peritoneal lavage, spleen and kidney from C57BL/6J mice treated two weeks before with 1×$10^{11}$ AAV-rsmCD6 (n=8) or AAV Luc (n=8) viral particles. Data are expressed as mean±SD of cfu×$10^3$/mL or mg, and statistical comparisons made by using the 2-tailed Student t-test.

Prophylactic Effect of Liver-Specific AAV-Mediated Expression of Mouse Soluble CD6 in CLP-Induced Septic Shock In order to achieve high and sustained circulating levels of soluble CD6, a recombinant AAV8 was engineered to express a mouse sCD6 form (AAV-rmsCD6) under the transcriptional control of a liver-specific promoter. The rationale behind not using the human but the msCD6 was that the latter would be less immunogenic for mice and its long-term expression and function would not be interfered by newly appearing neutralizing antibodies. Transduction of C57BL/6 mice with AAV-rsmCD6 virus resulted detectable rmsCD6 in plasma from day 10 on, reaching maximal levels at days 15 to 20 (FIG. 4A). This expression system allowed sustained expression levels of rmsCD6 in the range of 5-15 μg/mL for periods of time longer than three months. According to these results, mice were subjected to CLP-induced septic shock two weeks after transduction with $1 \times 10^{11}$ viral particles of AAV-rmsCD6 or control AAV-Luc, and their survival was monitored over time. As illustrated by FIG. 4B, mice treated with AAV-rmsCD6 showed a statistical significant higher survival rate (42.85%, n=14; P=0.0145) compared with control mice treated with AAV-Luc (7.14%, n=13). This effect was concomitant with significant reductions in serum levels of pro-inflammatory cytokines (TNF-α, IL-1β and IL-6), and increments in those of IL-10 (FIG. 4C). Similarly, bacterial load from blood, peritoneum, spleen and kidney was also reduced in the AAV-rmsCD6 group compared to controls (AAV-Luc), although differences only achieved statistical significance in peritoneum and spleen (FIG. 4D).

Example 2. Comparative Effects of the Co-Administration of CD6 Product with Broad-Spectrum Antibiotics in the Treatment and Prevention of CLP-Induced Sepsis Effects of Imipenem/Cilastatin Plus rshCD6 in CLP-Induced Sepsis The therapeutic effect of combining rshCD6 and the broad-spectrum bactericidal carbapenem Imipenem/Cilastatin—a treatment for critically ill patients with sepsis—on mouse survival post-CLP, was investigated. To this end, mice subjected to CLP were i.p. infused at +1 h with rshCD6 (1.25 mg/kg), Imipenem/Cilastatin (33 mg/kg/8 h) or a combination of the two. As illustrated by FIG. 2E, both rshCD6 (26.4%, n=34; P=0.008) and Imipenem/Cilastatin (19%, n=21; P=0.03) given alone, showed similar significant effects on mouse survival compared to the saline-treated group. Importantly, the simultaneous administration of rshCD6 plus Imipenem/Cilastatin showed at least additive effects on mouse survival (37.5%, n=24), which were statistically significant not only when compared with the saline treated group (P<0.0001) but also with the group treated with only Imipenem/Cilastatin (P=0.032).

Similarly, therapeutic infusion of Imipenem/Cilastatin (33 mg/kg/8 h, i.p.) at +1 h post-CLP, induced significant increments of mouse survival in both the AAV-rsmCD6 (42.85%, n=14 vs 78.57%, n=14) and AAV-Luc (7.14%, n=13 vs 56.25%, n=16) treated groups (FIG. 4B).

Figure 7:
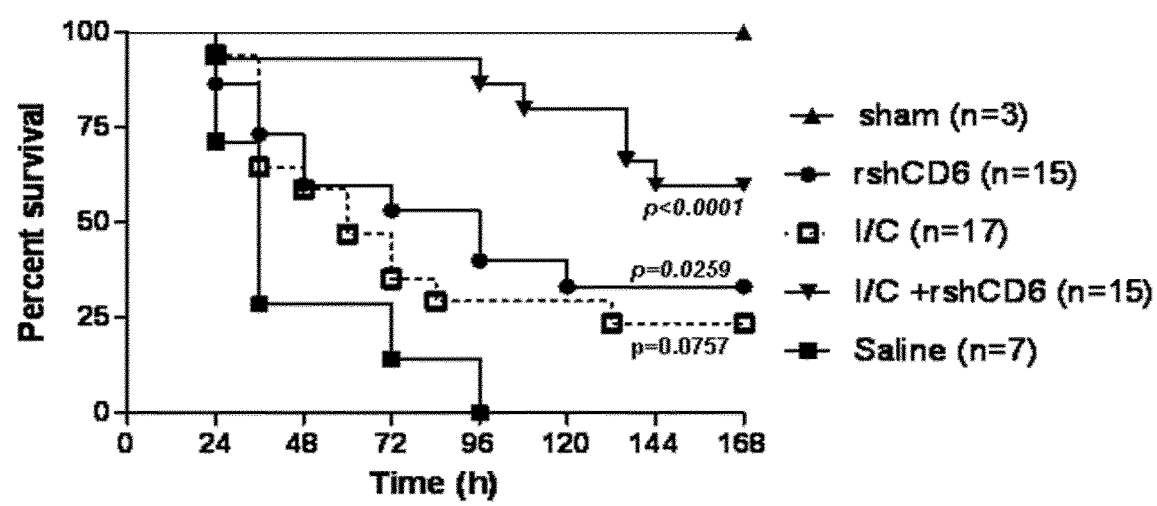

Importantly, the additive effects of rshCD6 plus Imipenen/Cilastatin infused via i.p. at +1 h post-CLP on mouse survival were extended by administering rshCD6 via the i.v. route at the same dose and time point. As shown in FIG. 7, mouse survival achieved by individual administration of Imipenem/Cilastatin (33 mg/kg/8 h; i.p.) (23.5%, n=17, P=0.017) or rshCD6 (1.25 mg/kg; i.v.) (33.3%, n=15; P=0.006) was greatly improved by their combined administration (60%, n=15; P=0.0001) compared with the saline-treated group. Importantly, the differences in mouse survival observed between groups receiving Imipenen/Clilastatin alone or combined with rshCD6 were also statistically significant (P=0.008). These effects would be indicative of different mechanisms of action for the two treatments.

Non-Additive Effects of Erythromycin Plus rshCD6 in CLP-Induced Sepsis

Figure 5:
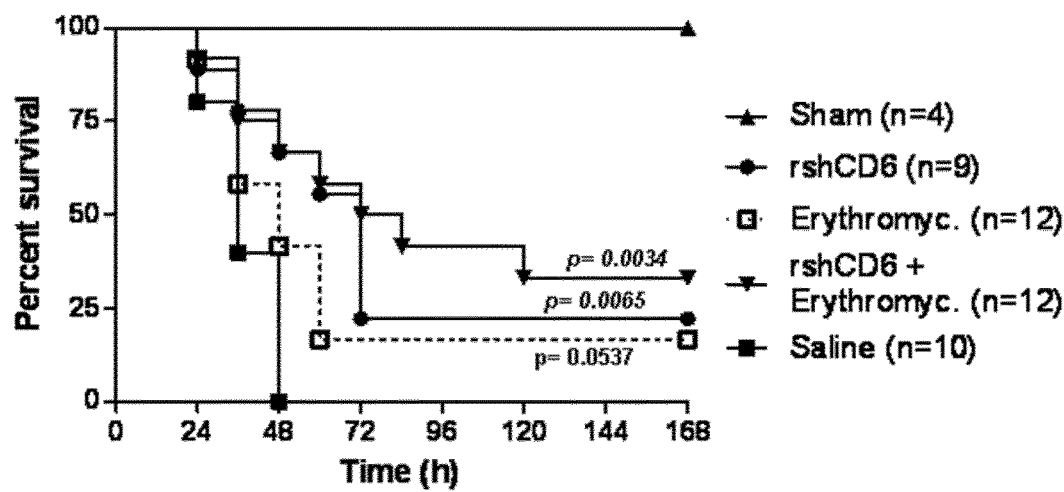
FIG. 5. Therapeutic efficacy of i.p. rshCD6 and/or Erythromycin infusion on CLP-induced polymicrobial septic shock. C57BL/6J mice (8-10 week old) were infused via i.p. with saline (n=10), rshCD6 (1.25 mg/kg), Erythromycin (2.75 μg/kg/8 h) or a combination of the two later (n=12) at time +0 h (A, top) or +1 h (B, bottom) post CLP-induced septic shock. Average survival was analyzed over time for each group and statistically compared to the saline-treated group using the long-rank t-test FIG. 6. Therapeutic efficacy of i.p. rshCD6 and/or Meropenem infusion on CLP-induced polymicrobial septic shock. C57BL/6J mice (8-10 week old) were infused via i.p. with saline, rshCD6 (1.25 mg/kg), Meropenem (17 mg/kg/8 h) or a combination of the two later (n=15) at time +0 h (A, top) or +1 h (B, bottom) post CLP-induced septic shock. Average survival was analyzed over time for each group and statistically compared to the saline-treated group using the long-rank t-test FIG. 7. Therapeutic efficacy of i.v. rshCD6 and/or i.v. Imipenem/Cilastatin infusion on CLP-induced polymicrobial septic shock. C57BL/6J mice (8-10 week old) were infused via i.v. with saline (n=14), rshCD6 (1.25 mg/kg) at +1 h (n=15), i.p. with Imipenem/Cilastatin (33 mg/kg/8 h, n=17) or a combination of the two later (n=15) post CLP-induced septic shock. Average survival was analyzed over time for each group and statistically compared to the saline-treated group using the long-rank t-test.
Figure 5:
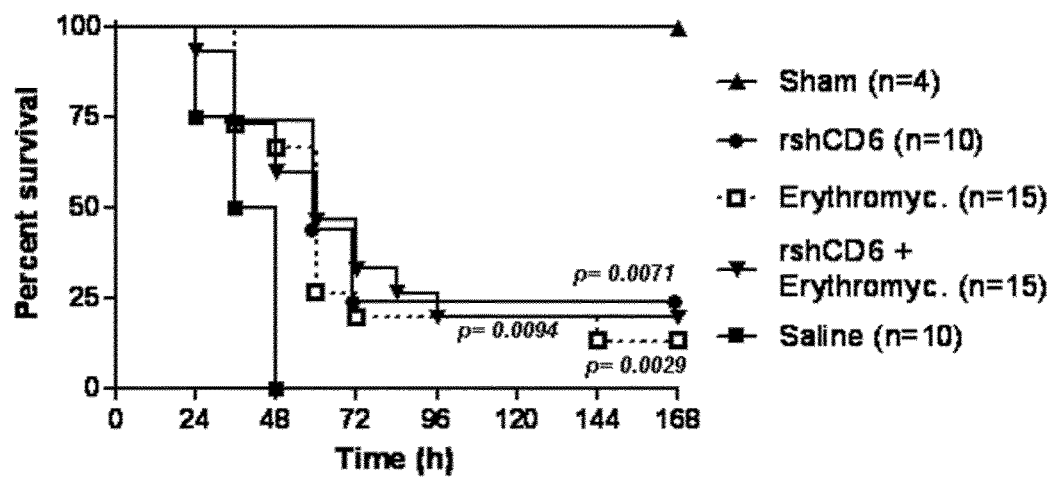

The therapeutic efficacy of rshCD6 and/or Erythromycin infusion on mouse survival post CLP-induced septic shock was analyzed in C57Bl/6 mice. As illustrated by FIG. 5A, a single infusion of either rshCD6 (1.25 mg/kg, n=9) or Erythromycin (2.75 μg/kg/8 h, n=12) via i.p. at time +0 h post-CLP, showed statistical significant effects on mouse survival (22.2%, P=0.0065, and 16.6%, P=0.054, respectively) when compared to the saline treated group (0%, n=10). Similar statistical significant results were obtained when rshCD6 and Erythromycin were given in combination (33.3% n=12; P=0.0034,). However, there were no statistically significant differences when the combination group was compared with the single therapy groups.

A very similar situation was observed when the same therapies were administered at +1 h post-CLP induction. As illustrated in FIG. 5B, a single infusion of either rshCD6 (1.25 mg/kg, n=10) or Erythyromycin (2.75 μg/kg/8 h, n=15) via i.p. at +1 h post-CLP, showed statistical significant effects on mouse survival (20%, P=0.0071, and 13.3%, P=0.0029, respectively) when compared with the saline treated group (0%, n=8). Similar statistically significant results were obtained when rshCD6 and Erythromycin were infused as combined compounds (20% n=15, P=0.0094). However, there were no significant differences between single and combined therapy groups.

Non-Additive Effects of Meropenem Plus rshCD6 in CLP-Induced Sepsis

Figure 6:
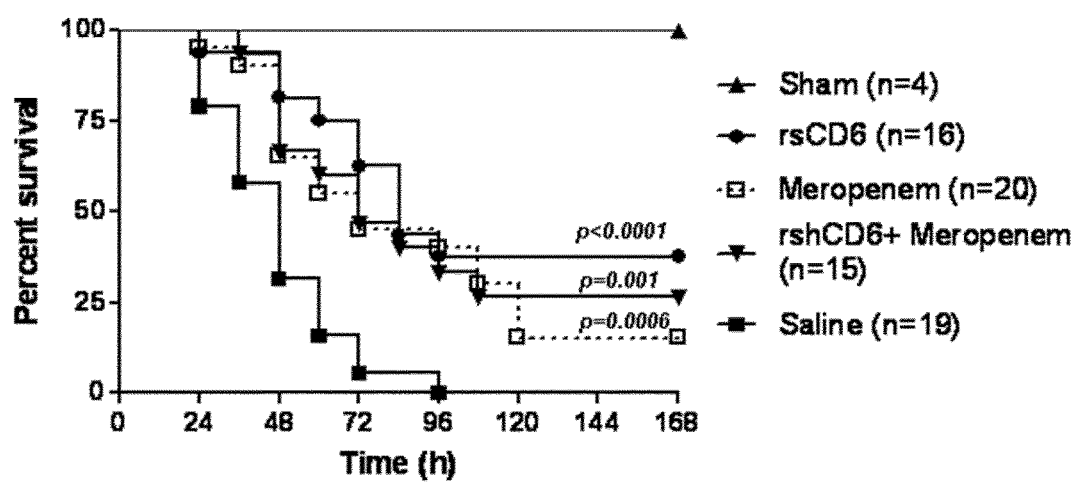
Figure 6:
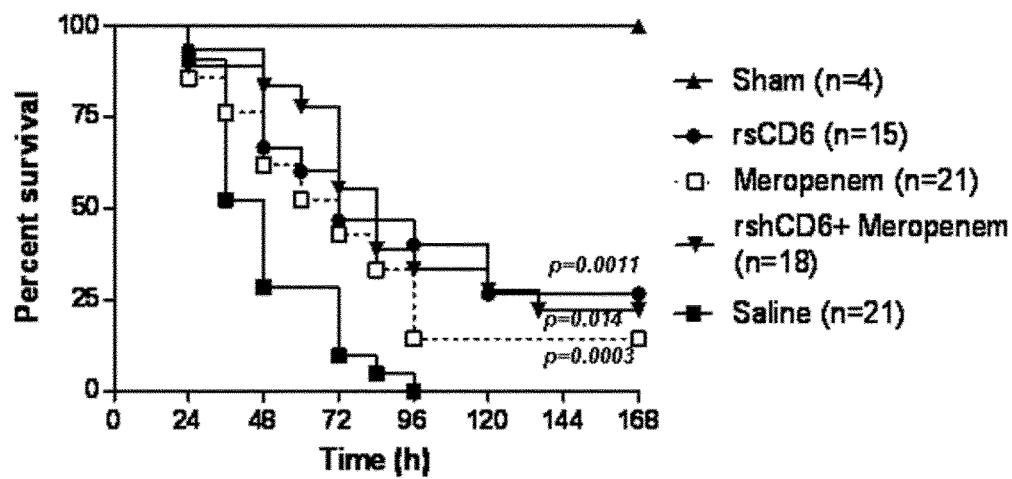

The therapeutic efficacy of rshCD6 and/or Meropenem infusion on mouse survival post CLP-induced septic shock was analyzed in C57Bl/6 mice. As illustrated by FIG. 6A, a single infusion either rshCD6 (1.25 mg/kg, n=16) or Meropenem (17 mg/kg/8 h, n=20) via i.p. at +0 h post-CLP, showed statistical significant effects on mouse survival (37.5%, P<0.0001, and 15%, P=0.0006, respectively) when compared to the saline treated group (0%, n=19). Similar results were obtained when rshCD6 and Meropenem were infused as combined compounds (26.6% n=15, P=0.001,). However, there were no significant differences between single and combined therapy groups.

Meropenem+rshCD6 vs Meropenem p=0.15

A very similar situation was observed when the same therapies were administered at +1 h post-CLP induction. As illustrated by FIG. 6B, a single infusion of either rshCD6 (1.25 mg/kg i.v., n=15) or Meropenem (17 mg/kg/8 h i.p., n=21) at +1 h post-CLP, showed statistical significant effects on mouse survival (26.7%, P=0.0011, and 14.28%, P=0.01, respectively compared with the saline treated group (n=21). Significant results were obtained when rshCD6 and Meropenem were infused as combined compounds (P=0.0003, 22.2% n=18). No significant differences were observed between single therapy groups and combined therapy.

Non-Additive Effects of Erythromycin Plus rshCD6 in CLP-Induced Sepsis

The therapeutic efficacy of rshCD6 and/or Erythromycin infusion on mouse survival post CLP-induced septic shock was analyzed in C57Bl/6 mice. As illustrated by FIG. 5A, a single infusion of either rshCD6 (1.25 mg/kg, n=9) or Erythromycin (2.75 µg/kg/8 h, n=12) via i.p. at time +0 h post-CLP, showed statistical significant effects on mouse survival (22.2%, P=0.0065, and 16.6%, P=0.054, respectively) when compared to the saline treated group (0%, n=10). Similar statistical significant results were obtained when rshCD6 and Erythromycin were given in combination (33.3% n=12; P=0.0034,). However, there were no statistically significant differences when the combination group was compared with the single therapy groups.

A very similar situation was observed when the same therapies were administered at +1 h post-CLP induction. As illustrated in FIG. 5B, a single infusion of either rshCD6 (1.25 mg/kg, n=10) or Erythromycin (2.75 µg/kg/8 h, n=15) via i.p. at +1 h post-CLP, showed statistical significant effects on mouse survival (20%, P=0.0071, and 13.3%, P=0.0029, respectively) when compared with the saline treated group (0%, n=8). Similar statistically significant results were obtained when rshCD6 and Erythromycin were infused as combined compounds (20% n=15, P=0.0094). However, there were no significant differences between single and combined therapy groups.

Discussion

Accordingly, the present Examples show the in vivo prophylactic and therapeutic effects of the soluble ectodomain from the scavenger-like lymphocyte receptor CD6 (sCD6), in a lethal model of polymicrobial infection of intra-abdominal origin. The results show time- and dose-dependent effects of sCD6 infusion on mouse survival post-CLP induction, which are concomitant to reduced systemic inflammatory response and bacterial load. Interestingly, both human and mouse sCD6 infusion showed improved effects on mouse survival when combined with the broad-spectrum bactericidal antibiotic Imipenem/Cilastatin.

Previous studies have indicated that sCD6 mainly acts through direct binding to key pathogenic factors from G− (LPS) and G+ (LTA and PGN) bacterial cell walls, and consequently interferes with TLR2- and TLR4-mediated cytokine release induced by them, aside from reducing bacterial growth and viability (Florensa M, et al., 2014. Targeting of key pathogenic factors from gram-positive bacteria by the soluble ectodomain of the scavenger-like lymphocyte receptor CD6. J Infect Dis 209:1077-1086). Such a broad bacterial binding properties makes sCD6 a suitable candidate for treating complex polymicrobial infections as it the case of that induced by CLP. In this model, a massive seeding of indigenous gut flora (mainly bacteria, from anaerobic to facultative aerobic or aerobic) into peritoneum and systemic circulation, develops the symptoms characteristic of peritonitis and sepsis, allowing testing the broad-spectrum antibacterial properties of sCD6.

Notwithstanding, PAMPs targeted by sCD6 are conserved constituents of bacterial cell walls, which are essential for bacterial survival and are not easily amenable to mutation without losing viability and/or pathogenicity. All these properties, makes sCD6 a good target for alternative/adjunctive antibacterial strategies, which would be effective even in the case of bacterial strains resistant to antibiotics.

The results show the induction of both prophylactic and therapeutic effects of sCD6 infusion, and how they are influenced by the route of administration. By using the i.p. route, the best results are achieved in the prophylactic mode (at −1 h pre-CLP), although therapeutic effects were still observed at early (+1 h) but not later (+3 h) time points post-CLP. Interestingly, the use of the i.v. route allowed extending the therapeutic effects of sCD6 up to +3 h or +6 h post-CLP.

When co-administering Imipenem/Cilastatin with sCD6 (via i.p. or i.v.) at least clear additive therapeutic effects were evidenced.

Unexpectedly, the at least additive therapeutic effect of sCD6 was not observed when combined with other broad-spectrum antibiotics from the same (Meropenem) or different (Erythromycin) class. This would indicate that the observed at least additive effect is specific for Imipenem and cannot be systematically extended to other antibiotics.

Lifelong broad-spectrum antibiotics are also suitable choice for prophylaxis or treatment of infections in some clinical settings such as congenital or acquired immune deficiencies. However, clinicians must balance the benefits of prophylactic antibiotic usage with problems such compliance, adverse reactions and development of antibiotic resistance. In light of these circumstances, the prophylactic effects achieved by inducing sustained sCD6 plasma levels through liver-specific AAV-mediated expression could be considered for clinical interventions.

In order to minimize immunogenicity-related problems related with human proteins, AAV virus coding for mouse sCD6 were used. This allowed to demonstrate that both human and mouse sCD6 share similar antibacterial properties, which have been conserved through evolution.

In conclusion, the results of the present examples show that sCD6 targeting is a feasible adjunctive strategy to Imipenem antibiotic therapy.

Items of the Present Invention—

The present invention provides the following items:

1. A composition comprising a CD6 product, or a derivative thereof, and Imipenem.

2. A pharmaceutical composition comprising the composition according to item 1 together with pharmaceutically acceptable carriers, pharmaceutically acceptable salts, adjuvants and/or suitable excipients.

3. A kit-of-parts comprising a CD6 product, or a derivative thereof, and Imipenem.

4. The composition according to any one of items 1 or 2, or the kit-of-parts according to item 3, wherein the CD6 product is a recombinant soluble CD6.

5. The composition according to any one of items 1 to 2, or 4, or the kit-of-parts according to any one of items 3 or 4, wherein the CD6 product is a human CD6 product.

6. The composition according to any one of items 1 to 2, or 4 to 5, or the kit-of-parts according to any one of items 3 to 5, wherein the CD6 product comprises the amino acid sequence SEQ ID NO: 1.

7. The composition according to any one of items 1 to 2, or 4 to 6, or the kit-of-parts according to any one of items 3 to 6, wherein the composition and/or kit-of-parts further comprises Cilastatin.

8. The composition according to any one of items 1 to 2, or 4 to 7, for use as a medicament.

9. The composition according to any one of items 1 to 2, or 4 to 7 for use in a therapeutic and/or preventive method of treatment, in a mammal including a human, of an infectious disease, or of an inflammatory condition related to an infectious disease, or of an inflammatory disease related to the presence of a product derived from an infectious agent.

10. The kit-of-parts according to any one of items 3 to 7 for simultaneous, sequential or separate use as a medicament.

11. The kit-of-parts according to any one of items 3 to 7 for simultaneous, sequential or separate use in a therapeutic and/or preventive method of treatment, in a mammal including a human, of an infectious disease, or of an inflammatory condition related to an infectious disease, or of an inflammatory disease related to the presence of a product derived from an infectious agent.

12. The composition for use according to any one of items 8 to 9, or the kit-of-parts for use according to any one of items 10 to 11, wherein the infectious disease is a microbial infection.

13. The composition or the kit-of-parts for use according to item 12, wherein the microbial infection is selected from the group consisting of a bacterial infection, a fungal infection, a viral infection, a parasitic infection, and combinations thereof.

14. The composition for use according to item 9, or the kit-of-parts for use according to item 11, wherein the infectious disease is a septicemia.

15. The composition or the kit-of-parts for use according to item 14, wherein the septicemia is selected from the group consisting of a bacteremia, a fungemia, a viremia, a parasitemia and combinations thereof.

16. The composition for use according to item 9, or the kit-of-parts for use according to item 11, wherein the infectious agent is selected from the group consisting of a bacterium, a fungus, a virus, a parasite, and combinations thereof.

17. The composition for use according to item 9, or the kit-of-parts for use according to item 11, wherein the inflammatory condition is systemic inflammatory response syndrome.

18. The composition for use according to item 9, or the kit-of-parts for use according to item 11, wherein the inflammatory condition is sepsis.

19. The composition or the kit-of-parts for use according to item 18, wherein the sepsis is polymicrobial sepsis.

20. The composition or the kit-of-parts for use according to item 18, wherein the sepsis is severe sepsis.

21. The composition or the kit-of-parts for use according to item 20, wherein the severe sepsis is septic shock.

22. The composition or the kit-of-parts for use according to item 21, wherein the septic shock is endotoxin-induced septic shock.

23. The composition or the kit-of-parts for use according to any one of items 9 to 22, wherein the composition is administered to a mammal including a human intravenously and/or intraperitoneally.

24. A CD6 product, or a derivative thereof, for use in a therapeutic and/or preventive method of treatment, in a mammal including a human, of an infectious disease, or of an inflammatory condition related to an infectious disease, or of an inflammatory disease related to the presence of a product derived from an infectious agent, wherein the method comprises simultaneously, sequentially or separately administering to a mammal including a human the CD6 product, or a derivative thereof and Imipenem.

25. The CD6 product, or a derivative thereof, for use according to item 24, wherein the CD6 product is a recombinant soluble CD6.

26. The CD6 product, or a derivative thereof, for use according to item 24, wherein the CD6 product is a human CD6 product.

27. The CD6 product, or a derivative thereof, for use according to item 24, wherein the CD6 product comprises the amino acid sequence SEQ ID NO: 1.

28. The CD6 product, or a derivative thereof, for use according to item 24, wherein the method further comprises the administration of Cilastatin.

29. Imipenem for use in a therapeutic and/or preventive method of treatment, in a mammal including a human, of an infectious disease, or of an inflammatory condition related to an infectious disease, or of an inflammatory disease related to the presence of a product derived from an infectious agent, wherein the method comprises simultaneously, sequentially or separately administering to a mammal including a human Imipenem and a CD6 product, or a derivative thereof.

The invention claimed is:

1. A method for therapeutic treatment of an infectious disease, an inflammatory condition related to an infectious disease or an inflammatory disease related to the presence of a product derived from an infectious agent, the method comprising administering a composition comprising a CD6 product, or a derivative thereof, or an isoform thereof, and Imipenem to a mammal in need thereof,
   wherein there is an at least additive effect for the combined administration of the CD6 product and imipenem with respect to their administration as single agents.

2. The method according to claim 1, wherein:
   i) the infectious disease is a microbial infection;
   ii) the inflammatory condition is systemic inflammatory response syndrome or sepsis;
   iii) the infectious agent is selected from the group consisting of a bacterium, a fungus, a virus, a parasite, and combinations thereof; or
   iv) a combination of any two or more of i), ii) and iii).

3. A method for therapeutic treatment of an infectious disease, an inflammatory condition related to an infectious disease or an inflammatory disease related to the presence of a product derived from an infectious agent, wherein the method comprises simultaneously, sequentially or separately administering to a mammal in need thereof a CD6 product, or a derivative thereof, or an isoform thereof and Imipenem,
   wherein there is an at least additive effect for the combined administration of the CD6 product and imipenem with respect to their administration as single agents.

4. The method according to claim 3, wherein the method further comprises administering Cilastatin.

5. The method according to claim 1, wherein the mammal is a human.

6. The method according to claim 1, wherein the infectious disease is a septicemia.

7. The method according to claim 1, wherein the CD6 product is a recombinant soluble CD6 product.

8. The method according to claim 7, wherein the CD6 product is a human recombinant soluble CD6 product.

9. The method according to claim 1, wherein the CD6 product, or a derivative thereof, or an isoform thereof, comprises the amino acid sequence SEQ ID NO: 1.

10. The method according to claim 1, wherein the composition further comprises Cilastatin.

11. The method according to claim 3, wherein the mammal is a human.

12. The method according to claim 3, wherein:
i) the infectious disease is a microbial infection;
ii) the inflammatory condition is systemic inflammatory response syndrome or sepsis;
iii) the infectious agent is selected from the group consisting of a bacterium, a fungus, a virus, a parasite, and combinations thereof; or
iv) a combination of any two or more of i), ii) and iii).

13. The method according to claim 3, wherein the CD6 product, or a derivative thereof, or an isoform thereof, comprises the amino acid sequence SEQ ID NO: 1.

14. The method according to claim 1, wherein the CD6 product or a derivative thereof, or an isoform thereof and Imipenem are administered parenterally.

15. The method according to claim 3, wherein the CD6 product or a derivative thereof, or an isoform thereof and Imipenem are administered parenterally.

16. The method according to claim 1, wherein the CD6 product or a derivative thereof, or an isoform thereof and Imipenem are administered intravenously.

17. The method according to claim 3, wherein the CD6 product or a derivative thereof, or an isoform thereof and Imipenem are administered intravenously.

* * * * *